(12) United States Patent
Delcayre et al.

(10) Patent No.: US 7,704,964 B2
(45) Date of Patent: Apr. 27, 2010

(54) METHODS AND COMPOUNDS FOR THE TARGETING OF PROTEIN TO EXOSOMES

(75) Inventors: Alain Delcayre, San José, CA (US); Jean-Bernard Le Pecq, Menlo Park, CA (US)

(73) Assignee: Exothera L.L.C., Menlo Park, CA (US)

( * ) Notice: Subject to any disclaimer, the term of this patent is extended or adjusted under 35 U.S.C. 154(b) by 840 days.

(21) Appl. No.: 10/485,360

(22) PCT Filed: Aug. 14, 2002

(86) PCT No.: PCT/EP02/09108

§ 371 (c)(1), (2), (4) Date: Jan. 30, 2004

(87) PCT Pub. No.: WO03/016522

PCT Pub. Date: Feb. 27, 2003

(65) Prior Publication Data

US 2004/0197314 A1    Oct. 7, 2004

Related U.S. Application Data

(60) Provisional application No. 60/313,159, filed on Aug. 17, 2001, provisional application No. 60/343,991, filed on Dec. 26, 2001.

(51) Int. Cl.
*A61K 31/70* (2006.01)
*C12N 15/74* (2006.01)
*C12N 15/09* (2006.01)
*A61N 63/00* (2006.01)

(52) U.S. Cl. ............ 514/44; 435/320.1; 435/455; 424/93.2; 424/93.21

(58) Field of Classification Search .............. None
See application file for complete search history.

(56) References Cited

U.S. PATENT DOCUMENTS 5,972,337 A * 10/1999 Ceriani et al. ............ 424/185.1

FOREIGN PATENT DOCUMENTS

| EP | 1 004 664 A | 5/2000 |
|---|---|---|
| FR | EP1004664 A1 * | 5/2000 |
| WO | 97/05900 | 2/1997 |
| WO | 98/10749 | 3/1998 |
| WO | WO 00/28001 A | 5/2000 |
| WO | WO 00/30667 * | 6/2000 |
| WO | 01/82958 | 11/2001 |
| WO | 02/00729 | 1/2002 |
| WO | 02/056831 | 7/2002 |
| WO | 03/016522 | 2/2003 |
| WO | 03/076603 | 9/2003 |

OTHER PUBLICATIONS

Denzer et al. (Exosome: from internal vesicle of the multivesicular body to intercellular signaling device. Journal of Cell Science, 2000. 113:3365-3374).*

Coulie et al. J Exp Med 1994;180:35-42.*

Thery et al; "Molecular Characterization of Dendritic Cell-Derived Exosomes, Selective Accumulation of the Heat Shock Protein HSC73"; The Journal of Cell Biology, Rockefeller University Press, US, vol. 147, No. 3, Nov. 1, 1999, pp. 599-610, XP000918507.

Oshima et al; "Secretion of a Peripheral Membrane Protein, MFG-E8, as a Complex With Membrane Vesicles"; European Journal of Biochemistry/FEBS., Germany, Feb. 2002, vol. 269, No. 4, pp. 1209-1218, XP002233407.

Andersen et al ;"Functional Analysis of two Cellular Binding Domains of Bovine Lactadherin"; Biochemistry, American Chemical Society, Easton, PA, US, vol. 39, No. 20, May 23, 2000, pp. 6200-6206, XP000917941.

* cited by examiner

*Primary Examiner*—Q. Janice Li
(74) *Attorney, Agent, or Firm*—Nixon & Vanderhye P.C.

(57) ABSTRACT

The present invention relates to compositions and methods for selectively expressing a polypeptide in a membrane vesicle. The invention also relates to genetic constructs and recombinant cells suitable to produce such membrane vesicles. This invention also relates to such functionalized membrane vesicles as well as to methods of making antibodies, methods of producing or regulating an immune response as well as to methods of screening or identifying binding partners using the same. The invention more particularly uses lactadherin or portions thereof to selectively express polypeptides in membrane vesicles, of natural or synthetic origin. This invention can be used in experimental, research, therapeutic, prophylactic or diagnostic areas.

38 Claims, 5 Drawing Sheets

METHODS AND COMPOUNDS FOR THE TARGETING OF PROTEIN TO EXOSOMES

Figure 1:
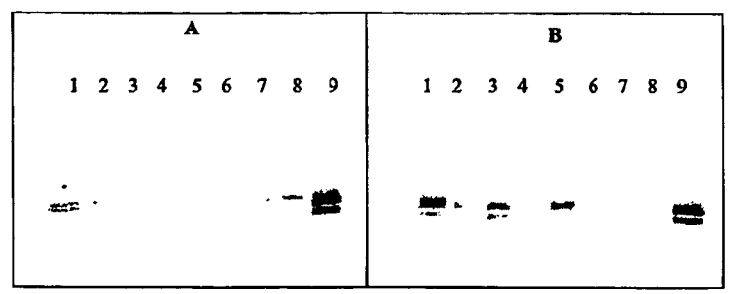

This application is the U.S. national phase of international application PCT/EP02/09108, filed in French on 14 Aug. 2002, which designated the U.S. PCT/EP02/09108 claims priority to U.S Application No. 60/313,159 filed 17 Aug. 2001 and U.S Application No. 60/343,991 filed 26 Dec. 2001. The entire contents of these applications are incorporated herein by reference.

The present invention relates to compositions and methods for selectively expressing a polypeptide in a membrane vesicle. The invention also relates to genetic constructs and recombinant cells suitable to produce such membrane vesicles. This invention also relates to such fuctionalized membrane vesicles as well as to methods of making antibodies, methods of producing or regulating an immune response as well as to methods of screening or identifying binding partners using the same. The invention more particularly uses lactadherin or portions thereof to selectively express polypeptides in membrane vesicles, of natural or synthetic origin. This invention can be used in experimental, research, therapeutic, prophylactic or diagnostic areas.

BACKGROUND

Exosomes are vesicles of endosomal origin that are secreted in the extracellular milieu following fusion of late endosomal multivesicular bodies with the plasma membrane (4). Cells from various tissue types have been shown to secrete exosomes, such as dendritic cells, B lymphocytes, tumor cells and mast cells, for instance. Exosomes from different origin exhibit discrete sets of proteins and lipid moieties (5,6). They notably contain proteins involved in antigen presentation and immuno-modulation suggesting that exosomes play a role in cell-cell communications leading to the modulation of immune responses. Indeed, exosomes from dendritic cells (DC) pulsed with peptides derived from tumor antigens elicit anti-tumor responses in animal model using the matching tumor (7,8). Methods of producing, purifying or using exosomes for therapeutic purposes or as research tools have been described for instance in WO99/03499, WO00/44389 and WO97/05900, incorporated therein by reference.

Considering their immunogenic and therapeutic properties, it would be particularly useful to be able to modify the content of exosomes in order to alter their properties. In this respect, recombinant exosomes have been described in the art, which derive from cells transfected with plasmids encoding recombinant proteins. Such recombinant exosomes contain the plasmid-encoded recombinant protein (WO00/28001).

SUMMARY OF THE INVENTION

The present invention now discloses novel methods of producing recombinant exosomes. The invention also discloses methods of selectively expressing a polypeptide in exosomes. The invention also describes novel chimeric molecules and recombinant cells containing the same, which can be used to produce such recombinant exosomes. This invention also relates to such functionalized membrane vesicles as well as to methods of making antibodies, methods of producing or regulating an immune response as well as to methods of screening or identifying binding partners using the same.

Figure 2:
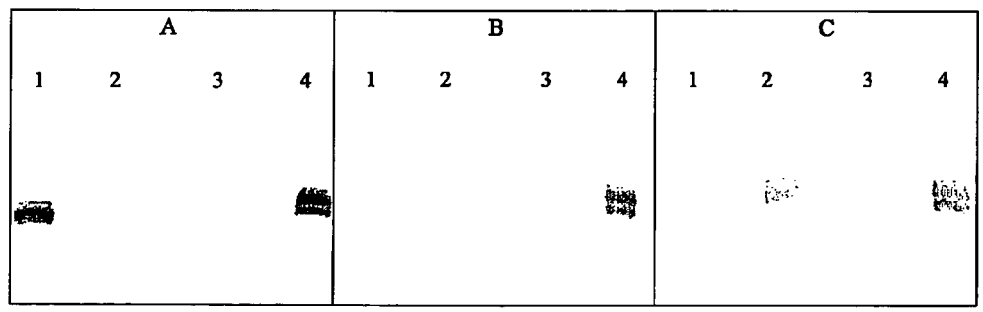
Figure 3:
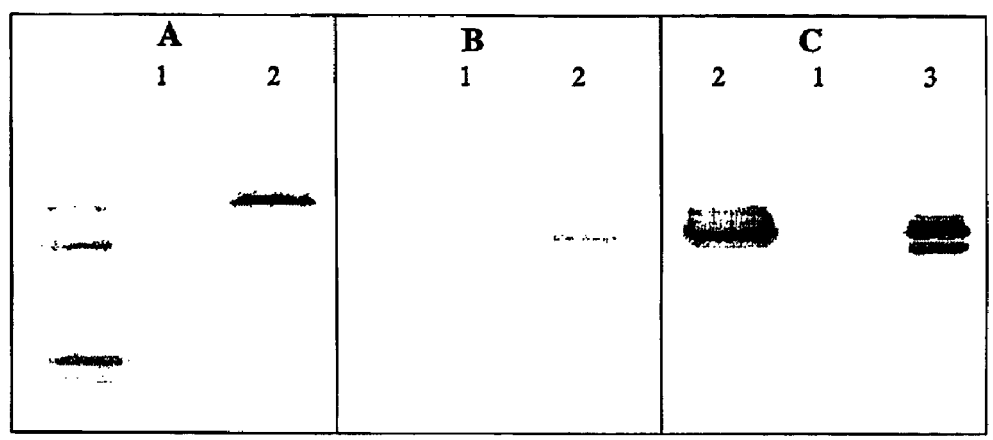

The present invention is based on the unexpected findings that Lactadherin is expressed in many exosome-producing cells and that in these cells, Lactadherin is almost exclusively found associated with exosomes (FIG. 1). This highly specific subcellular localiation occurs for endogenous Lactadherin but also for exogenous Lactadherin following transfection of exosome-producing cells with a plasmid encoding Lactadherin (FIG. 2). We found that by deleting specific short portions of the C1/C2 domain of Lactadherin, the subcellular localization of Lactadherin is changed (FIG. 2). These findings strongly support that the C1/C2 domain of Lactadherin contains a highly specific targeting motif for exosome surfaces and that the modification of the C1/C2 domain of Lactadherin changes the specificity of targeting towards other surfaces. We found that his phenomenon is conserved across several species since in vitro transfection of exosome-producing cell lines from mice and hamster with a plasmid encoding human recombinant Lactadherin also yields human recombinant Lactadherin almost exclusively associated to mouse and hamster exosomes, respectively (FIG. 3). Moreover, mouse recombinant Lactadherin expressed in hamster cell lines is also found in hamster exosomes (FIG. 3).

Emanating from this, the introduction into a protein of part or the entirety of the C1 and/or C2 domain of Lactadherin or a functional equivalent thereof allows the targeting of the resulting chimeric protein to exosomes and other lipidic structures.

The invention further discloses methods allowing the identification of additional targeting polypeptides or genes, which can be used to construct chimeric genes or proteins for targeting or expression into exosomes. These chimeric proteins can be used to generate recombinant vesicles tailored to acquire new desirable functions. Given the intrinsic properties of exosomes, i.e. immunogenicity and non-toxicity, the resulting recombinant exosomes represent a novel tool for numerous applications in research and medical fields. Notably, the potency of exosomes to induce strong immune responses render them ideal tools to prepare antibodies against antigens expressed on recombinant exosomes. Also, biologically active chimeric proteins can be used to generate recombinant exosomes tailored to acquire new therapeutic properties. The unexpected ability of Lactadherin to target polypeptides and to be expressed selectively in exosomes also provides novel approaches to the purification of such polypeptides, including Lactadherin itself.

An object of this invention thus resides in a method of targeting polypeptides to exosomes, comprising:
a) Providing a chimeric genetic construct encoding said polypeptide fused to a targeting polypeptide comprising Lactadherin or a portion thereof comprising a functional C1 and/or C2 domain; and
b) Introducing said construct into exosome-producing cells in vivo or ex vivo to generate recombinant exosomes.

An other object of this invention is a method of selectively expressing a polypeptide at the surface of exosomes, comprising:
a) Providing a chimeric genetic construct encoding said polypeptide fused to Lactadherin or a portion thereof comprising a functional C1 and/or C2 domain;
b) Introducing said constuct into exosome-producing cells to generate recombinant exosomes, and
c) Collecting said recombinant exosomes, wherein said exosomes carry at their surface polypeptides encoded by said chimeric genetic construct.

A further object of this invention is a method of preparing functionalized exosomes, comprising:
a) Providing a chimeric genetic construct encoding a polypeptide fused to Lactadherin or a portion thereof comprising a functional C1 and/or C2 domain;

b) Introducing said construct into exosome-producing cells to generate functionalized exosomes presenting said polypeptide at their surface, and c) Collecting and/or purifying said functionalized exosomes.

An other object of this invention is a method of producing a polypeptide comprising Lactadherin or a portion thereof, the method comprising:

a) Providing a genetic construct encoding said polypeptide;

b) Introducing said construct into exosome-producing cells to generate functionalized exosomes presenting said polypeptide at their surface, c) Collecting and/or purifying said functionalized exosomes, and d) Recovering and/or purifying said polypeptide or a fragment thereof from said functionalized exosomes.

Still a further object of this invention is a functionalized exosome prepared by the above methods as well as compositions comprising such functionalized exosomes and a pharmaceutically acceptable excipient or carrier.

This invention also relates to chimeric genetic constructs encoding a polypeptide of interest fused to a targeting moiety comprising the C1 and/or C2 domain of lactadherin or an other targeting polypeptide as identified below. The polypeptide of interest may be for instance an antigen, a cytokine, a ligand, a receptor, an immunoglobulin, a marker polypeptide, an enzyme, an ionic channel, or a portion thereof. Specific examples of such chimeric genes encode a polypeptide selected from SEQ ID NO: 22-27, 32 or 33 or a fragment thereof devoid of the 8 C-terminal amino acid residues.

This invention further encompasses a vector comprising a chimeric genetic construct as described above, as well as recombinant cells comprising a chimeric genetic construct or a vector as described above.

The invention also provides methods to identify or screen exosome-targeting polypeptides as well as methods to generate chimeric proteins that are selectively targeted to membrane vesicles (e.g., exosomes). The chimeric proteins are typically composed of a polypeptide sequence (e.g., the complete or partial sequence of naturally occurring protein such as antigens, cytoldnes, ligands, receptors or immunoglobulins) fused to the sequence of a targeting polypeptide, typically Lactadherin or a portion thereof including a functional C1 and/or C2 domain, preferably a functional C1/C2 domain thereof.

A further aspect of this invention thus resides in a method of screening, identification or selection of exosome-targeting polypeptides, the method comprising:

providing a first genetic construct encoding a candidate polypeptide, preferably a candidate trans-membrane polypeptide;

introducing the first genetic construct into exosome-producing cells and testing expression of the candidate polypeptide into exosomes;

selecting a candidate polypeptide which is expressed in exosomes and preparing a second genetic construct encoding said selected polypeptide fused to a trans-membrane antigen or receptor;

introducing the second genetic construct into exosome-producing cells and testing expression of the fusion polypeptide into exosomes; and selecting the polypeptide which causes efficient expression of the trans-membrane antigen or receptor into exosomes.

Our results show that different proteins or polypeptides which contain specific targeting signals directing expression on exosomes can be identified, selected and/or improved using the above methods. These polypeptides require both the ability to be expressed into exosomes and to target other molecules to such vesicles. These polypeptides may be derived from transmembrane proteins, and may include all or a portion of such proteins, typically a portion comprising at least the trans-membrane domain. These constructs are particularly suited for the delivery of antigens to exosomes, particularly receptors and trans-membrane proteins. The method can be used to select specific, individual targeting polypeptides, or to screen libraries of genetic constructs.

The resulting recombinant exosomes can be used for many research and therapeutic applications including raising antibodies, generating exosomes with improved therapeutic properties, antigen delivery and library screening to identify counterparts of protein-protein interactions.

The present invention can also be used advantageously to create synthetic lipid vesicles. Indeed, the invention can be used to target molecules to lipid structures other than exosomes such as any naturally occurring vesicle or organelle comprising a plasma membrane bilayer as well as synthetic vesicles comprising lipids such as liposomes or any synthetic particles with hydrophobic properties. Such lipid vesicles are preferably engineered to contain (or be enriched in) phosphatidyl-serine and/or other lipids naturally contained in exosomes in order to allow efficient targeting and binding of the chimeric molecule.

Furthermore, the invention can be used to deliver any selected molecule artificially fused to lactadherin or a portion thereof. In this regard, the invention is not limited to genetic fusions but also encompasses chemical fusions, i.e., any chemical (covalent) complex of a lactadherin and a molecule.

LEGEND TO THE FIGURES

FIG. 1: Targeting of Lactadherin to exosomes.

FIG. 2: Targeting of exogenous lactadherin to exosomes.

FIG. 3: Selective expression of Lactadherin is conserved across species.

Figure 4:
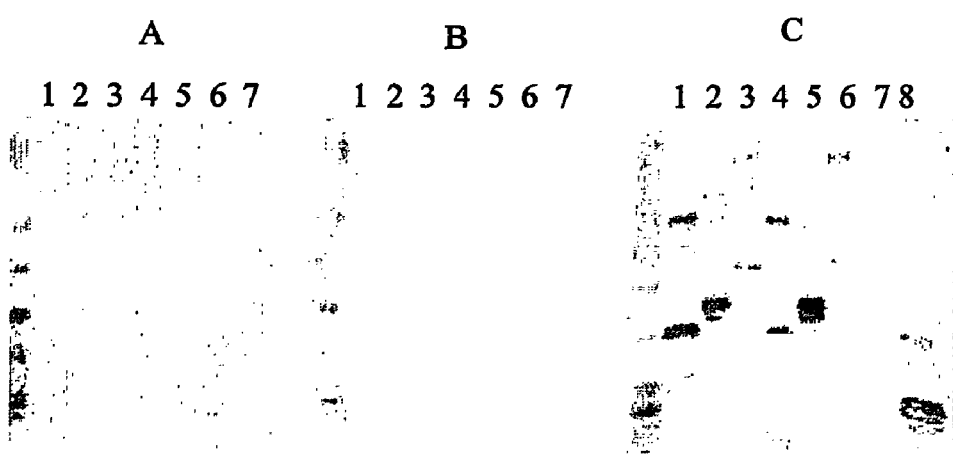

FIG. 4: Selective Expression in exosomes of Biologically active IL2 fused to Lactadherin.

Figure 5:

FIG. 5: Purification of recombinant human lactadherin.

Figure 6:
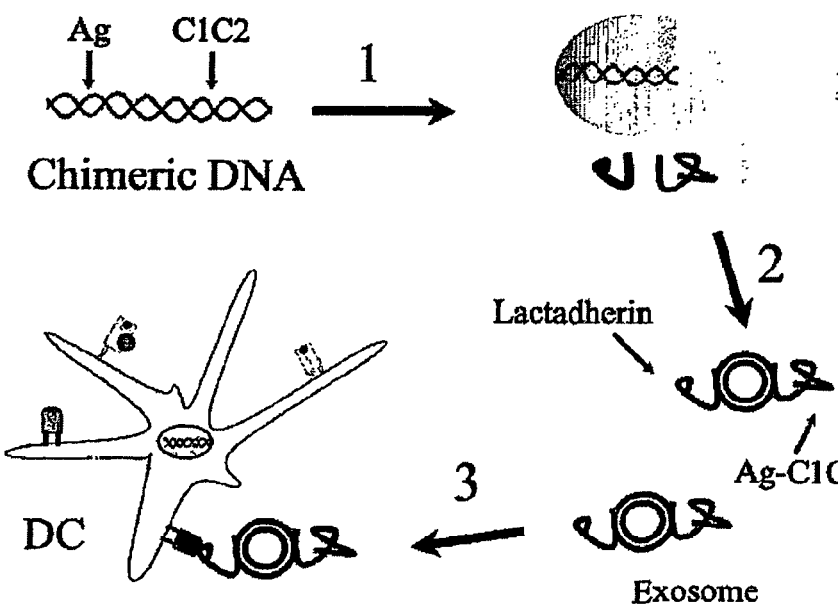

FIG. 6: Cross-priming of APCs upon DNA vaccination.

Figure 7:
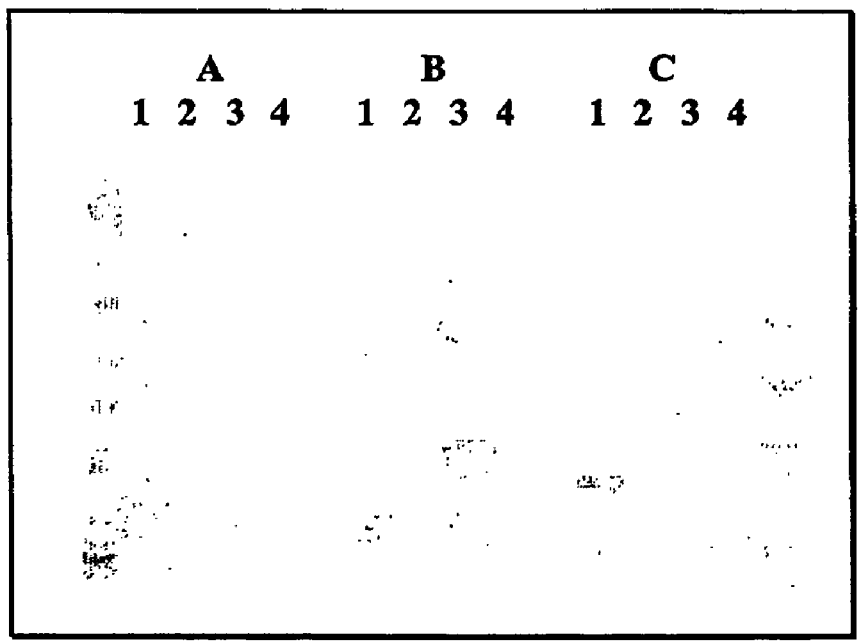

FIG. 7: Expression of recombinant candidate trans-membrane polypeptides into exosomes. Recombinant MelanA/MART1 (Panel A), CD40L (Panel B) and CD81 (Panel C) were detected in exosomes and also in cell lysates of transfected cells.

Figure 8:
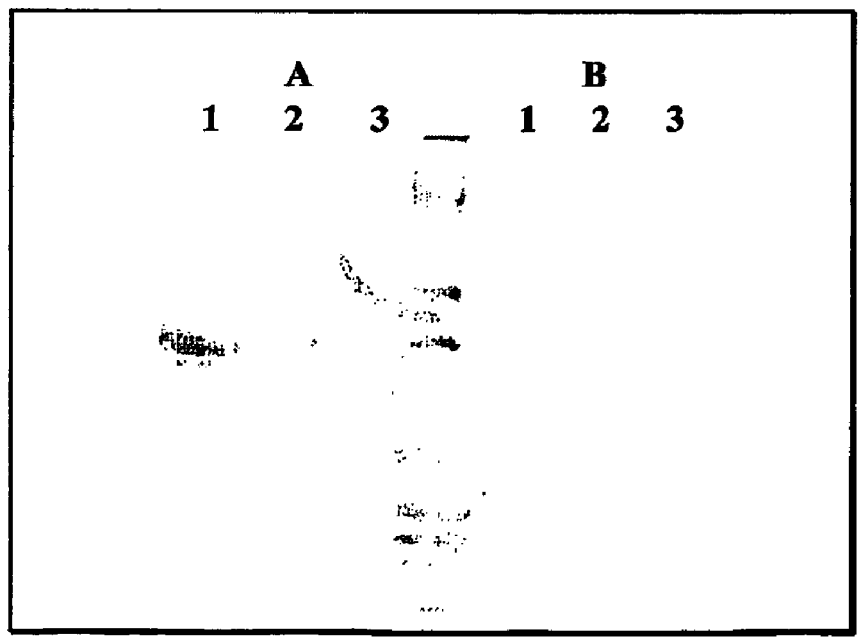

FIG. 8: Expression of recombinant chimeric proteins into exosomes.

Figure 9:
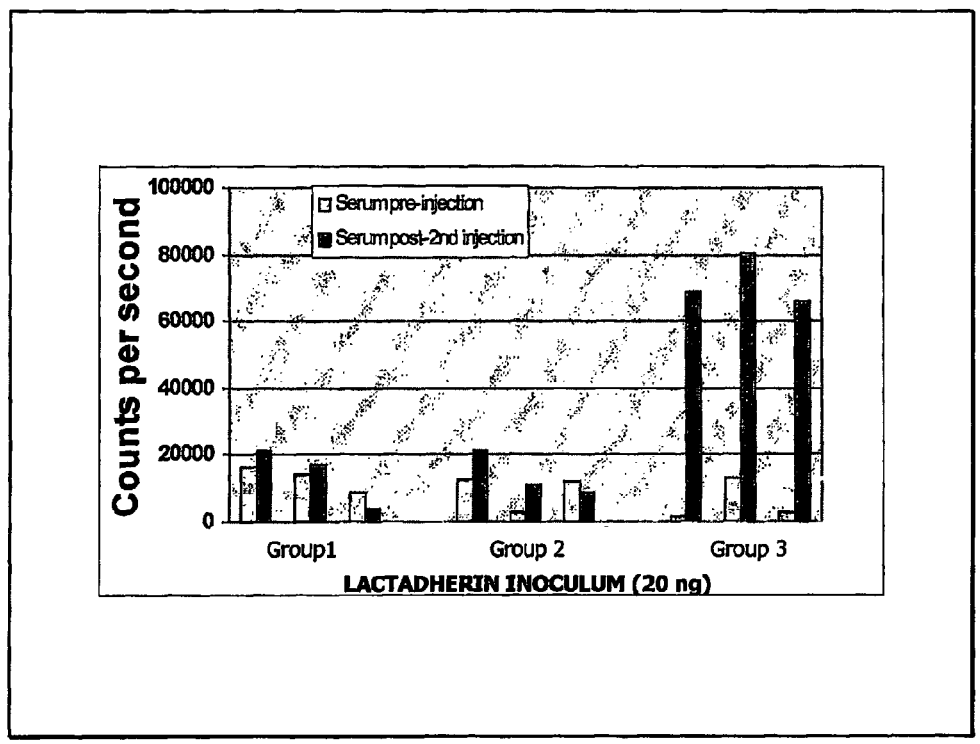

FIG. 9: Detection of anti-lactadherin antibodies in the serum of mice immunized with lacdherin-containing exosomes.

DETAILED DESCRIPTION OF THE INVENTION

The present invention discloses novel methods of producing recombinant exosomes and their uses. The invention more particularly uses a targeting polypeptide, such as lactadherin or portions thereof, to selectively express or to target polypeptides in membrane vesicles, of natural or synthetic origin. This invention can be used in experimental, research, therapeutic, prophylactic or diagnostic areas.

The present invention stems from the discovery of novel unexpected properties of lactadherin. More particularly, the invention shows that lactadherin is selectively expressed in exosomes and can be used to selectively express polypeptides in such vesicles.

As indicated above, this invention provides methods of targeting or (selectively) expressing polypeptides in exosomes, methods of functionalizing exosomes, and methods of producing polypeptides, which methods use a chimeric gene or genetic construct encoding a chimeric polypeptide. The chimeric polypeptide comprises a polypeptide of interest fused to lactadherin or functional domains thereof.

Lactadherin

Lactadherin is a protein that was first identified in breast tissue. It is a component of milk where it associates with several other proteins at the surface of milk fat globules. Lactadherin comprises an epidermal-growth factor-like (EGF-like) domain in its N-terminal extremity that contains the sequence motif Arginine-Glycine-Aspartic acid (R-G-D) found in integrin ligands. This motif mediates the binding of Lactadherin to $\alpha_v\beta_3$ and $\alpha_v\beta_5$ integrins. The C-terminal extremity of Lactadherin contains a C1/C2 domain that is involved in the interaction of Lactadherin with milk fat globules. Several other proteins that bind to other cell surfaces have related C1/C2 domains. The C1/C2 domain of Lactadherin has been shown to preferentially bind to surfaces containing phosphatidyl-serine lipids (Ref. 1 to 3). Lactadherin has been shown to be present at the surface of exosomes produced by murine dendritic cells. In this regard, WO00/30667 relates to the use of lactadherin or variants thereof to deliver antigens to dendritic cells or to mediate an immune response in vivo. U.S. Pat. No. 5,455,031 discloses the cloning of the long form of human lactadherin.

The present invention stems from the discovery of novel unexpected properties of lactadherin, i.e., the ability of lactadherin to selectively express or target polypeptides in exosomes.

Within the context of this invention, the term "selectively" indicates that the lactadherin (or chimeric polypeptide) which is expressed by the cells is present almost exclusively at the surface of exosomes, although residual or minor presence in other cell compartments or membranes may be observed. The invention is partly based on the unexpected determination that lactadherin is predominantly expressed at the surface of exosomes and can be used to produce exosomes or lipid vesicles enriched for desired molecules attached to lactadherin.

Within the context of this invention, the term exosomes (or vesicles) that "carry" a molecule at their surface designates vesicles that contain such molecules attached to their membrane. The molecule may be exposed outside of the vesicle, or contained within the vesicle (i.e., attached to the inner side of the membrane). Typically, the invention allows efficient presentation of the molecule at the surface of vesicles, i.e., their exposure outside of the vesicle.

In performing the present invention it is possible to use lactadherin from various sources or origins. Typically, it is preferred to use a mammalian lactadherin or a portion thereof. Mammalian lactadherin includes human, murine, rat, bovine, porcine and equine lactadherin, for instance. Most preferred lactadherin is human or murine, or fragments or functional equivalents thereof.

In this regard, the invention preferably uses:
(i) human lactadherin or murine lactadherin,
(ii) a fragment of human lactadherin or murine lactadherin comprising a functional C1 and/or C2 domain, more preferably a functional C1/C2 domain, or
(iii) a polypeptide comprising at least 50% primary structure identity with the polypeptides of (i) or (ii).

The amino acid sequence of human lactadherin is depicted SEQ ID NO: 7 (long form) and 8 (short form). Examples of corresponding nucleic acid molecules are represented in SEQ ID NO: 5 and 6, respectively. The amino acid sequence of murine lactadherin is depicted SEQ ID NO: 10. See also Stubbs et al. (PNAS 87(21), 1990, 8417), as well as Genbank Accession no. M38337.

In a particular embodiment of this invention, the chimeric gene comprises a lactadhern having an amino acid sequence comprising SEQ ID NO: 7, 8, 10 or a fragment thereof comprising a functional C2 domain.

In an other particular embodiment of this invention, the chimeric gene comprises a lactadherin having an amino acid sequence comprising SEQ ID NO: 7, 8, 10 or a fragment thereof comprising a functional C1 domain.

In a further particular embodiment, the chimeric gene comprises a lactadherin having an amino acid sequence comprising a functional C1/C2 domain of SEQ ID NO:7,8 or 10.

The C2 domain of human lactadherin is comprised in amino acid residues 229-387 of SEQ ID NO:7. The C1 domain of human lactadherin is comprised in amino acid residues 69-225 of SEQ ID NO:7. In a typical example, the chimeric construct encodes at least amino acid residues 229-387 or 69-225 of SEQ ID NO:7. In a further particular embodiment, the chimeric construct encodes at least amino acids 69-387 of SEQ ID NO: 7.

The C2 domain of murine lactadherin is comprised in amino acid residues 271-426 of SEQ ID NO:10. The C1 domain of murine lactadherin is comprised in amino acid residues 111-266 of SEQ ID NO:10. In a typical example, the chimeric construct encodes at least amino acid residues 111-266 or 271-426 of SEQ ID NO:10. In a further particular embodiment, the chimeric construct encodes at least amino acids 111-426 of SEQ ID NO: 10. In an other particular embodiment, the chimeric construct encodes at least amino acids 109-426 of SEQ ID NO: 10.

As indicated above, the targeting moiety may be a polypeptide comprising at least 50% primary structure identity with the polypeptides of (i) or (ii) above. Identity may be determined according to various known techniques, such as by computer programs, preferably be the CLUSTAL method. More preferably, the targeting polypeptide has at least 60% identity, advantageously at least 70% identity with the polypeptides of (i) or (ii). Such lactadherin variant (or functional equivalent) should retain the ability to target polypeptides to exosomes. This property may be verified as described in the examples, e.g., by creating a chimeric gene comprising said variant fused to a marker polypeptide, expressing the same in an exosome-producing cell and determining the presence of the marker polypeptide at the surface of the exosome. Preferred lactadherin variants have at least 85% identity with the polypeptides of (i) or (ii) above. Possible variations include amino acid deletion(s), substitution(s), mutation(s) and/or addition(s).

Specific examples of such variants or functional equivalents include other C1/C2 domain-containing polypeptides or proteins, or fragments thereof. In particular, specific examples of such functional variants include Del-1, Neuropilin-1, coagulation factor 5 and coagulation factor 8 or fragments thereof comprising a functional C1 and/or C2 domain thereof.

Screening of Targeting Polylpeptides

The present invention also discloses that additional, efficient targeting polypeptides can be produced, screened and/or isolated. In particular, this invention shows that polypeptides can be selected for their expression in exosomes and for their capacity to deliver other polypeptides to such vesicles. The invention shows that polypeptides which are naturally expressed in exosomes do not necessarily represent efficient targeting polypeptides, while polypeptides which are not naturally expressed in these vesicles can be produced artificially and cause efficient delivery of polypeptides of interest. The invention also shows that polypeptides which are not normally expressed into exosomes can be forced into such compartments, by recombinant DNA technologies.

Although exosome-specific proteins that are found exclusively on exosomes, such as Lactadherin, are preferred for the targeting of proteins to exosomes, proteins that are enriched in exosomes or non-exclusive to exosomes are also potential candidates for the targeting of other proteins to exosomes. The invention now provides a means to identify and use such candidates. Illustrating this, we have found that recombinant MelanA/MART1, CD40L and CD81 are expressed in exosomes following transfection of cells with plasmids encoding these trans-membrane molecules. These results are described in Example 6. MelanA/MART1 is a tumor associated intracellular membrane protein that was recently found in exosomes derived from tumor cells. It was suggested that this occurrence reflects the ability of exosomes to transfer full-length tumor antigens to APC (9). Our findings show that MelanA/MART1 is in fact an integral component of exosomes derived from MelanA/MART1$^+$ tumor exosomes. CD40L is an important stimulator of immune responses and our findings showing that it can be detected on exosomes are unprecedented. In contrast, CD81 is a known component of exosomes and has previously been shown to be enriched in B cell-derived exosomes. We constructed chimeric proteins including MelanA/MART1 or CD81 fused to a seven-transmembrane receptor, CCR7, and found that MelanA/MART1-CCR7 chimeric protein is almost exclusively expressed in exosomes, whereas CCR7 alone is only detected on the cell surface. In contrast, and surprisingly, the CD81 chimeric construct with CCR7 did not yield any detectable protein (See Example 6), despite the fact that CD81 is naturally expressed by exosomes. Hence our method shows that efficient exosome-targeting polypeptides exist and allows the identification and selection of such polypeptides that can be used to target antigens, and notably transmembrane antigens and receptors to exosomes.

A further aspect of this invention thus resides in a method of screening, identification or selection of exosome-targeting polypeptides, the method comprising:

providing a first genetic construct encoding a candidate polypeptide, preferably a candidate trans-membrane polypeptide;

introducing the first genetic construct into exosome-producing cells and testing expression of the candidate polypeptide into exosomes;

selecting a candidate polypeptide which is expressed in exosomes and preparing a second genetic construct encoding said selected polypeptide fused to a targeted polypeptide;

introducing the second genetic construct into exosome-producing cells and testing expression of the fusion polypeptide into exosomes; and selecting the polypeptide which causes efficient expression of the targeted polypeptide into exosomes.

Our results show that different proteins or polypeptides which contain specific targeting signals directing expression on exosomes can be identified, selected and/or improved using the above methods. These polypeptides require both the ability to be expressed into exosomes and to target other molecules to such vesicles. These polypeptides may be derived from transmembrane proteins, and may include all or a portion of such proteins, typically a portion comprising at least the trans-membrane domain. These constructs are particularly suited for the delivery of antigens to exosomes, particularly receptors and trans-membrane proteins.

Preferably, the targeting polypeptide is or comprises a trans-membrane domain. Candidate targeting polypeptides may be derived from virtually any protein comprising such a trans-membrane domain, such as receptors, channels, etc. Specific examples of such targeting polypeptides include MelanA/MART1, CD40L, CD81, etc., or a portion thereof. The targeting polypeptide may comprise an entire trans-membrane protein, or only a portion thereof comprising at least one trans-membrane domain.

Because of the nature of the candidate targeting polypeptide, the method is essentially suited for identification of polypeptides adapted for delivering trans-membrane polypeptides to exosomes, or for delivering polypeptides inside exosomes. Most preferred targeted polypeptides are thus trans-membrane polypeptides, such as receptors, trans-membrane antigens, or portions thereof. The invention is particularly advantageous since it allows the screening of targeting polypeptides allowing efficient expression of complex molecules, such as receptors having several trans-membrane domains (e.g., G-Protein Coupled Receptors or "GPCR"), into particular vesicles.

Expression of the candidate targeting polypeptide or of the fusion polypeptide into exosomes can be tested according to various techniques, which are disclosed throughout the entire description of this application. In a preferred embodiment, a genetic construct is introduced into exosome-producing cells, exosomes are prepared from said modified cells, and expression of the polypeptide within said exosomes is measured. Expression can be measured by a variety of techniques, including using specific ligands of the targeting or targeted polypeptides. In a specific example, expression is measured using antibodies specific for the targeting moiety or for a tag sequence introduced within the fusion polypeptide.

In preparing the fusion polypeptide, the targeted moiety may be placed either upstream or downstream from the targeting polypeptide, i.e., either in C-ter or in N-ter. The orientation of the fusion determines the type of expression of the targeted polypeptide. In particular, coupling of the targeted polypeptide to the intracellular portion of the targeting polypeptide will cause expression of the targeted polypeptide inside of the vesicle (for soluble antigens). On the other hand, for expression of trans-membrane receptors, the type of coupling is adjusted by the skilled person depending on the construct, to allow proper folding and insertion into the exosome membrane.

As will be disclosed later, coupling can be either direct or via a spacer molecule, and the exosome-producing cells may be of various source and origin.

Also, different fusions may be expressed and tested, either in parallel or in the same vesicles. In this regard, the method can be used to select specific, individual targeting polypeptides, or to screen libraries of genetic constructs.

The method allows the production of improved targeting polypeptides and fusion molecules, which are highly efficient for expression into exosomes.

In this respect, the invention also relates to a method of producing an exosome expressing a selected trans-membrane polypeptide, the method comprising:

selecting a targeting polypeptide as described above, providing a genetic construct encoding the selected trans-membrane polypeptide fused to the targeting polypeptide, expressing the genetic construct into exosome-producing cells, and producing and isolating exosomes from said modified cells.

The invention also relates to a method of producing an exosome expressing a GPCR or a portion thereof comprising at least one trans-membrane domain, the method comprising:

providing a genetic construct encoding the GPCR or portion thereof fused to a targeting polypeptide comprising a trans-membrane domain and/or selected as described above, expressing the genetic construct into exosome-producing cells, and producing and isolating exosomes from said modified cells which express the GPCR or portion thereof.

The invention also relates to exosomes expressing a recombinant GPCR or a portion thereof.

The invention also relates to a fusion polypeptide comprising a targeting polypeptide selected from Melan/MART1, CD40L and CD81 and a targeted polypeptide. More preferably, the targeted polypeptide comprises a trans-membrane domain. The invention also relates to any polynucleotide sequence encoding such fusion polypeptides. Specific, illustrative examples of such fusions are provided as SEQ D NO: 32 and 33.

Polypeptide of Interest

The present invention can be used to target, selectively express, or produce (e.g., purify) various polypeptides in (from) exosomes or other lipidic structures, such as antigens, cytolines, ligands, receptors, immunoglobulins, a marker polypeptide (e.g., a label protein, such as Green Fluorescent Protein, or an enzyme, for instance), enzymes, ionic channels, etc., or a portion thereof. Generally, this invention can be used with any polypeptide of interest, e.g., any polypeptide having biological or immune properties. Furthermore, the invention can be used to simultaneously express or target several distinct chimeric genetic constructs encoding distinct polypeptides into exosomes, to further expand the scope of activities or reconstitute complex molecules.

Preferred examples of polypeptides are antigens, such as tumor antigens, viral antigens and microbial antigens, for instance. Illustrative examples of tumor antigens are MAGE, BAGE, Prostate tumor antigens, oncogenes, etc. The amino acid sequence of these antigens are known per se and can be produced by recombinant techniques or by synthesis. Particular antigens to be targeted or presented with this invention include soluble antigens and extracellular domains of receptors.

Further examples of polypeptides of interest include lymphokines IL2, IL4, IL-13), trophic factors (TNF, IFN, GM-CSF, G-CSF, etc.), enzymes, clotting factors, hormones, lipoproteins, etc.

An other type of polypeptides of interest is a receptor having at least one trans-membrane domain, more preferably a GPCR or a portion thereof. Indeed, the invention now allows the targeting and expression of trans-membrane polypeptides into particular vesicles using targeting polypeptides. The expression of GPCRs within vesicles allows their purification, characterization, the screening for ligands (whether synthetic or natural), the production of antibodies, etc. A specific example of a GPCR is, for instance, CCR7, although the invention can be used as well with other receptors.

Other particular examples are immunoglobulins and fragments thereof, such as for instance Fc fragments of immunoglobulins. Such Fc fragments, when expressed at the surface of exosomes, can act to target the exosomes to cells expressing receptors for such Pc fragments, such as antigen-presenting cells. The expression of such Fc fragments, either alone or in combination with the expression of antigens, facilitates and enhances exosome recognition by antigen-presenting cells, particularly dendritic cells, and increases cross-priming of such antigens.

Obviously, the invention is also adapted for the delivery of therapeutic proteins or polypeptides. Such proteins may be delivered to specific cells using fictionalized recombinant exosomes or liposomes, optionally with tissue-specific ligands at their surface. Thereby, therapeutic proteins may be expressed at the surface of cell lacking the endogenous protein or expressing a non-functional endogenous protein leading to pathologic conditions. In this regard, a specific object of this invention is a method of delivering a therapeutic protein to a subject comprising:

(a) Providing a chimeric genetic construct encoding said protein fused to Lactadherin or a portion thereof comprising a functional C1 and/or C2 domain, or to a targeting polypeptide identified using a method as disclosed above;

(b) Introducing said construct into exosome-producing cells to generate recombinant exosomes carrying said chimeric proteins at their surface, (c) Collecting said recombinant exosomes and injecting said exosomes or a portion thereof to said patient.

Furthermore, because the invention also allows chemical coupling of molecules to Lactadherin or functional equivalents thereof, the invention also extends to non-polypeptide compounds such as small molecules, nucleic acids, lipids, saccharides, glycolipids, etc.

As indicated, the invention now makes it possible to express on exosomes a combination of various molecules through their targeting with Lactaderin or functional equivalents thereof, so as to reconstitute artificially particles having increased immunogenicity. A typical example is a combination of antigen(s), Lactadherin, targeting polypeptide (e.g. Fc fragment) and/or adjuvant (e.g., cytokine, including GM-CSF, etc.).

Fusion

Chimeric polypeptides or compounds can be prepared by genetic or chemical fusion.

For the genetic fusion, the region of the chimeric gene coding for the polypeptide of interest may be fused upstream, downstream or at any internal domain junction of Lactadherin or a targeting polypeptide. In this regard, the examples demonstrate that upstream fusions with lactadherin are functional, as well as N-ter and C-ter fusions with targeting polypeptides. Furthermore, the domains may be directly fused to each other, or separated by spacer regions that do not alter the properties of the chimeric polypeptide. Such spacer regions include cloning sites, cleavage sites, flexible domains, etc. In addition, the chimeric genetic construct may further comprise a leader signal sequence to favor secretion of the encoded chimeric polypeptide into the endoplasmic reticulum of exosome-producing cells. Generally, the chimeric gene comprises the lactadherin leader sequence. However, it is possible to insert heterologous leader sequences, especially where portions of lactadherin are used. Moreover, the chimeric gene may further comprise a tag to facilitate purification or monitoring, such as a myc tag, a poly-histidine tag, etc.

For the chemical fusion, the partial or full-length lactadherin sequence may be selected or modified to present at its extremity a free reactive group such as thiol, amino, carboxyl group to cross-link a soluble polypeptide, a glycolipid or any small molecule. In a preferred embodiment, the Lactadherin construct encodes at least amino acids 1-230 of SEQ ID NO: 7 in which the C1 domain (amino acids 60-225) provides the targeting motif to exosomes and Cysteine 230 provides the free thiol-residue for chemical cross-linking to other molecules. Crosslinking peptides, chemicals to SH groups can be achieved through well established methods (review G. T. Hermanson (1996) Bioconjugate techniques San Diego Academic Press 785 pages). The advantage of this method is that it extends the scope of the invention to the preparation of antibodies to compounds other than polypeptides, such as glycolipids, drugs and organic chemicals. It also provides a means to target polypeptide and compounds to exosomes without introducing putative neo-antigenic determinants. Selected cross-linking reagents have been shown to be immunologicaly silent (G. T. Hermanson (1996) cited above). Neo-antigenic determinants sometimes occur at the junction of chimeric genes and may limit the usage of chimeric gene products for specific prophylactic and therapeutic human applications.

Modified exosomes or lipid vesicles (e.g., liposomes) can thus be prepared by producing exosomes (or liposomes) presenting the relevant lactadherin construct such as SEQ ID NO 7 and then reacting them with the product to be linked. Alternatively, the lactadherin fragment cross-linked to a product may be prepared and subsequently added to purified exosomes or liposomes.

Vectors

This invention further encompasses a vector comprising a chimeric genetic construct as described above, as well as recombinant cells comprising a chimeric genetic construct or a vector as described above. The vector may be a plasmid, a phage, a virus, an artificial chromosome, etc. Typical examples include plasmids, such as those derived from commercially available plasmids, in particular pUC, pcDNA, pBR, etc. Other preferred vectors are derived from viruses, such as replication defective retroviruses, adenoviruses, AAV, baculoviruses or vaccinia viruses. The choice of the vector may be adjusted by the skilled person depending on the recombinant host cell in which said vector should be used. In this regard, it is preferred to use vectors that can transfect or infect mammalian cells. Indeed, preferred recombinant host cells are mammalian cells. These can be primary cells or established cell lines. Illustrative examples include fibroblasts, muscle cells, hepatocytes, immune cells, etc., as well as their progenitor or precursor cells. Most preferred mammalian cells are exosome-producing mammalian cells. These include, for instance, tumor cells, dendritic cells, B and T lymphocytes or mastocytes.

Exosome-Producing Cells

Exosome-producing cells include any cell, preferably of mammalian origin, that produces and secretes membrane vesicles of endosomal origin by fusion of late endosomal multivesicular bodies with the plasma membrane (4). Cells from various tissue types have been shown to secrete exosomes, such as dendritic cells, B lymphocytes, tumor cells, T lymphocytes and mast cells, for instance. Methods of producing, purifying or using exosomes for therapeutic purposes or as research tools have been described for instance in WO99/03499, WO00/44389, WO97/05900, incorporated herein by reference. Preferred exosome-producing cells of this invention are mammalian tumor cells, mammalian T lymphocytes and mammalian dendritic cells, typically of murine or human origin. In this regard, the cells are preferably immortalized dendritic cells (WO94/28113), immature dendritic cells or tumor cells (WO99/03499). Furthermore, for the production of antibody, it may be advantageous to use B lymphocytes as exosome-producing cells, since the resulting exosomes comprise accessory functions and molecules such as MHC class II molecules that facilitate antibody-production. Furthermore, it has been shown that B cells-derived exosomes are able to bind to follicular dendritic cells, which is an other important feature for antibody induction (10).

The cells may be cultured and maintained in any appropriate medium, such as RPMI, DMEM, etc. The cultures may be performed in any suitable device, such as plates, dishes, tubes, flasks, etc.

The genetic construct (or vector) can be introduced into the exosome-producing cells by any conventional method, such as by naked DNA technique, cationinc lipid-mediated transfection, polymer-mediated transfection, peptide-mediated transfection, virus-mediated infection, physical or chemical agents or treatments, electroporation, etc. In this regard, it should be noted that transient transfection is sufficient to express the relevant chimeric gene so that it is not necessary to create stable cell lines or to optimize the transfection conditions. The exosomes produced by such cells may be collected and/or purified according to techniques known in the art, such as by centrifugation, chromatography, etc. Preferred techniques have been described in WO00/44389 and in US09/780,748, incorporated therein by reference.

The recombinant, functionalized exosomes of this invention can be used to produce antibodies, to regulate an immune response, to deliver a biological activity and/or as a screening tool, to select ligands of any selected polypeptide.

Preparation of Antibodies

In a particular embodiment, the present invention relates to the use of recombinant exosomes as described above to produce antibodies specific for any polypeptide or other antigen.

A considerable advantage of this invention is that antigens are associated with immuno-stimulatory components on recombinant exosomes, which allows the generation of antibodies against poorly immunogenic antigens and in situation where classical approaches to prepare antibodies failed. In particular, exosomes produced from B lymphocytes contain MHC II molecules that stimulate antibody production. Also, the preparation of antibodies can be achieved without the need to purify large amounts of antigens. In fact, a single and small scale purification method to isolate exosomes (US09/780,748) can be used regardless of the nature of the exogenous antigen expressed at their surface. Thus, the antigen preparation step can be completed very rapidly, i.e., typically within less than 12 hours. This method is rapid and can be performed on many samples in parallel allowing the simultaneous preparation of multiple antigens for immunization. The expression of antigens in a naturally occurring vesicle combined to a gentle purification procedure helps preserve the native conformation of antigens, which may enable the generation of relevant antibodies with potential therapeutic applications. Moreover, the invention generates lipid vesicles that contain a high density of chimeric molecules (e.g., antigen) at their surface. This high density can be compared to a polymeric state which highly favors antibody production by increasing antigen avidity. A further advantage of this invention is that the polypeptides can be expressed by exosome producing cells and thus subjected to natural pathways of processing and post-translational modifications (glycosylations, etc.).

The present invention thus also relates to methods of producing an antibody that binds a polypeptide, the method comprising immunizing a non-human mammal with functionalized exosomes as described above which express said polypeptide or an epitope thereof, and collecting antibodies or antibody-producing cells from said mammal. The method is particularly suited for producing antibodies to antigens fused to lactadherin, or to trans-membrane receptors fused to a targeting polypeptide, as described above.

The present invention also relates to methods of producing an antibody that binds a polypeptide, comprising:
(a) Providing a chimeric genetic construct encoding said polypeptide or an epitope thereof fused to Lactadherin or a portion thereof comprising a functional C1 and/or C2 domain;
(b) Introducing said construct into exosome-producing cells to generate recombinant exosomes presenting said polypeptide or epitope at their surface,
(c) Collecting said recombinant exosomes and injecting said exosomes or a portion thereof to a non-human mammal to generate antibodies that bind said polypeptide or epitope and,
(d) Collecting antibodies or antibody-producing cells from said mammal.

The present invention also relates to methods of producing an antibody that binds a receptor, such as a GPCR, comprising:
(a) Providing a chimeric genetic construct encoding said receptor or an epitope thereof fused to a targeting polypeptide;
(b) Introducing said construct into exosome-producing cells to generate recombinant exosomes presenting said receptor or epitope at their surface,
(c) Collecting said recombinant exosomes and injecting said exosomes or a portion thereof to a non-human mammal to generate antibodies that bind said receptor or epitope and,
d) Collecting antibodies or antibody-producing cells from said mammal.

The antibodies may be polyclonal or monoclonal. Methods of producing polyclonal antibodies from various species, including mice, rodents, primates, horses, pigs, rabbits, poultry, etc. may be found, for instance, in Vaitukaitis et al., 1971. Briefly, the antigen (in the present invention, the recombinant exosome) is injected in the presence or absence of an adjuvant (complete or incomplete adjuvant e.g., Freund's adjuvant) and administered to an animal, typically by sub-cutaneous, intra-peritoneal, intra-venous or intramuscular injection. Repeated injections may be performed. Blood samples are collected and immunoglobulins or serum are separated.

Methods of producing monoclonal antibodies may be found, for instance, in Harlow et al (Antibodies: A laboratory Manual, CSH Press, 1988) or in Kohler et al (Nature 256 (1975) 495), incorporated therein by reference. Briefly, these methods comprise immunizing an animal with the antigen (in the present invention, the recombinant exosome), followed by a recovery of spleen or lymph nodes cells which are then fused with immortalized cells, such as myeloma cells. The resulting hybridomas produce the monoclonal antibodies and can be selected by limit dilutions to isolate individual clones.

In a particular embodiment, the exosome-producing cells are B lymphocytes.

In an other particular embodiment, the exosome-producing cells and/or the lactadherin and/or the targeting polypeptide is (are) from the same species as the mammal used for immunization. Indeed, in such as system, the exosomes and lactadherin are not immunogenic and antibodies are produced essentially only against the selected antigen.

In a particular embodiment, the exosome-producing cells are murine cells, the lactadherin is a murine lactadherin or a portion or variant thereof comprising a functional C1 and/or C2 domain, the non-human mammal is a mouse, and the antigen or epitope is from a different species, for instance of human origin. Even more preferably, the mouse is a humanized mouse, allowing humanized antibodies to be produced.

To that effect, the nucleotide sequence of a protein (the antigen or an epitope) can be fused to the C1 and/or C2 domain of mouse Lactadherin and the resulting chimeric sequence is cloned into a eukaryotic expression vector using standard molecular biology techniques. Plasmids encoding the chimeric protein are transfected into an exosome-producing mouse cell line and recombinant exosomes are harvested after several days of culture of the transfected cells. Recombinant exosomes are then purified by centrifugation on a sucrose gradient (US09/780,748). The presence of chimeric proteins on recombinant exosomes is established by Western blot analysis using a monoclonal anti-C1/C2 domain antibody. Recombinant exosomes bearing chimeric proteins are then injected into syngeneic mice to generate antibodies. In this context, only the antigenic determinants contained in the protein sequences used to generate chimeric proteins represent foreign antigens in the immunized mice. The generation of antibodies is verified in screening assays designed according to the nature of the antigen. If recombinant exosomes are used in the screening assay, a second chimeric protein is prepared where the same protein antigen sequence is fused with an extended C1/C2 domain of Lactadherin sequence. Alternatively, recombinant exosomes expressing the protein antigen fused to the C1/C2 domain of Lactadherin from a different species can also be used. These new constructions create chimeric proteins with new junction sequences, thereby, avoiding the detection/selection of antibodies directed at the junction of the chimeric protein used for immunization.

As indicated above, this methods is very advantageous and can be used to produce antibodies in various species, against any selected antigen or epitope, including tumor antigens, bacterial antigens or viral antigens.

Preparation of Recombinant Exosomes that Display New Biological Activity

The present invention can be used to produce recombinant exosomes that exhibit any selected biological activity. These can be produced by targeting one (or several) polypeptides with particular biological activity to the surface of exosomes, as described above.

An advantage of this invention is that high local concentration of biologically active components may be reached on recombinant exosomes, which enable exosomes to acquire potent new biological activity with the possibility of cross-linking receptors on target cells. Such high local concentration also allows to increase the avidity of the carried molecule, thus improving the potency of the exosome. Also, this invention allows reconstituting biologically active multi-component entities on exosomes, thereby broadening the field of applications of recombinant exosome to multi-chain proteins when classical approaches to manipulate such proteins have been difficult.

An example of biologically active protein that can be used is Interleukin-2 (IL2), a cytokine that activates T cells and is used in cancer immunotherapy to stimulate T cell responses against tumor cells. The simultaneous presentation of this immunologically defined adjuvant with tumor antigens on exosomes may improve the efficiency of exosome. In this case, the functional assay to verify that IL2 on recombinant exosome is biologically active will use an IL2-dependent cell line.

Another example of biologically active protein is CD40 Ligand (CD40L) that induces helper signals required for DC to initiate an immune response against captured antigens. The simultaneous presentation of helper signal with tumor antigens on exosomes may improve the efficiency of exosome. In this case, a functional assay to monitor the induction of markers of activation on DC will be used to verify that CD40L on recombinant exosome is biologically active.

Further examples include other lymphokines (IL-4, IL-13), trophic factors (TNF, IFN, GM-CSF, G-CSF, etc.), enzymes, clotting factors, hormones, lipoproteins, etc.

Other particular examples are polypeptides that facilitate targeting or interaction of exosomes to or with particular cells, preferably with dendritic cells. Such targeting polypeptides include for instance Fc fragments of immunoglobulins. Such Fc fragments, when expressed at the surface of exosomes, can act to target the exosomes to antigen-presenting cells. The expression of such Fc fragments in combination with the expression of antigens (and, optionally, adjuvant molecule as disclosed above) factilitates and enhances exosome recognition by antigen-presenting cells, particularly dendritic cells, and increases cross-priming of such antigens.

To produce such functionalised exosomes, the full-length or partial cDNA sequences of biologically active proteins can be fused either upstream or downstream the sequence coding for a targeting polypeptide and the resulting chimeric sequence is cloned into a eukaryotic expression vector using standard molecular biology techniques. The targeting polypeptide may be selected or derived from C1 and/or C2 domain of human Lactadherin sequence or an equivalent thereof, and from targeting polypeptides identified using the above-disclosed screening method, such as MART1/MelanA or a fragment thereof. Plasmids encoding the chimeric protein are transfected into an exosome-producing cell line and recombinant exosomes are harvested after several days of culture of the transfected cells. Recombinant exosomes are then purified by centrifugation on a sucrose gradient. The presence of chimeric protein on recombinant exosomes is established by Western blot analysis using antigen-specific antibodies (if available) and/or anti-targeting polypeptide antibodies. Functional assays are then performed to verify that the biological activity of the proteins fused to the targeting polypeptide is preserved. The functionalized exosomes may then be administered in vivo to any mammalian subject in need thereof, in particular human subject. Administration can be performed by various routes, such as by systemic injection, e.g., intraveinous, intramuscular, intra-peritoneal, intra-tumoral, sub-cutaneous, etc.

Delivery of Full-Length Antigens to DC using Recombinant Exosomes

In addition to the humoral or antibody response induced by recombinant exosomes, cellular immune responses can also be generated against antigen expressed on exosomes. Chimeric sequences including full-length cDNA encoding tumor or microbial antigens and the targeting polypeptide are prepared as described above. Recombinant exosomes can then be used directly to vaccinate individuals or indirectly to pulse DC in vitro. Delivery of full-length antigens to DC alleviates haplotypes restriction for vaccine usage. Also, delivery through a natural pathway of antigen uptake by and transfer to DC will yield efficient processing of antigen and presentation of both class I and II epitopes. Hence, recombinant exosomes expressing full-length tumor or microbial antigens may contribute to improved vaccines against cancer and infectious diseases.

A further object of this invention is a method of delivering an antigen to a subject comprising:
(a) Providing a chimeric genetic construct encoding said antigen fused to Lactadherin or a portion thereof comprising a functional C1 and/or C2 domain;
(b) Introducing said construct into exosome-producing cells to generate recombinant exosomes carrying said antigen at their surface,
(c) Collecting said recombinant exosomes and injecting said exosomes or a portion thereof to said subject.

An other object of this invention is a method of delivering an antigen to a subject comprising:
(a) Providing a chimeric genetic construct encoding said antigen fused to Lactadherin or a portion thereof comprising a functional C1 and/or C2 domain;
(b) Introducing said construct into exosome-producing cells to generate recombinant exosomes carrying said antigen at their surface,
(c) Collecting said recombinant exosomes and contacting the same ex vivo with dentritic cells from said subject and,
(d) injecting said contacted dendritic cells or a portion thereof to said subject.

A "portion" of dendritic cells indicates that it is possible to inject all the contacted DC or to inject a fraction thereof and keep the rest for further injection(s) or use(s), if needed. Furthermore, the term "portion" indicates that although whole cells may be administered, preparations derived therefrom may be injected as well, such as membrane extracts or exosomes produced by such dendritic cells.

The dendritic cells or their portion may be injected by several routes, such as by intra-venous, intra-arerial, intra-peritoneal, intra-tumoral, intra-muscular, etc., as described for instance in WO99/03499 incorporated therein by reference.

As indicated above, in particular embodiments, the exosome-producing cells may be contacted with additional chimeric genetic construct(s) encoding additional (accessory) molecules fused to Lactadherin or a portion thereof comprising a functional C1 and/or C2 domain, to generate recombinant exosomes carrying said molecules at their surface, in addition to the antigen. The molecules may be adjuvant, targeting polypeptides, Lactadherin, etc. Particular examples include Fc fragment of immunoglobulin, CD40 ligand, cytokines and GM-CSF. The various genetic constructs may be comprised in one vector or in several separate constructs, which may be contacted simulatenously or sequentially with the exosome-producing cells.

Production of Functionalised Synthetic Lipid Vesicles

Furthermore, as indicated above, the present invention can be used with various membrane vesicles, including natural vesicles (such as exosomes) or synthetic vesicles, such as liposomes. Liposomes are versatile tools in research and medicine. They are small artificial vesicles produced from natural phospholipids and cholesterol. Such vesicles are currently being used as drug carriers loaded with a great variety of molecules, including small drug molecules, proteins, nucleotides and plasmids. Hence, liposomes can be used for a large number of applications. Within the present invention, it is possible to target molecules (e.g., polypeptides, antigens, small molecules, etc.) to liposomes through a chimeric molecule as described above, and to administer such a functionalized vesicle in a subject.

Typically, the liposome should contain phosphatidyl serine or other lipids naturally contained in exosomes, to facilitate targeting of the lactadherin chimeric polypeptide.

In this regard, the invention relates to a method of producing antibodies comprising:
Providing a chimeric molecule comprising an antigen fused to Lactadherin or a portion thereof comprising a functional C1 and/or C2 domain;
contacting said chimeric molecule with a lipid vesicle containing phosphatidyl serine or other lipids naturally contained in exosomes to create fictionalized lipid vesicle presenting said antigen at their surface, and
immunizing a non-human mammal with such a functionalized lipid vesicle to produce antibodies that bind said antigen.

An other object of this invention is a method of delivering an antigen to a subject comprising:
Providing a chimeric molecule comprising an antigen fused to Lactadherin or a portion thereof comprising a functional C1 and/or C2 domain;
contacting said chimeric molecule with a lipid vesicle containing phosphatidyl serine or other lipids naturally contained in exosomes, to create functionalized lipid vesicle presenting said antigen at their surface, and
contacting said functionalized lipid vesicle ex vivo with dentritic cells from said subject in the presence of lactadherin and,
injecting said contacted dendritic cells or a portion thereof to said subject.

An other object of this invention is a method of delivering an antigen to a subject comprising:
Providing a chimeric molecule comprising an antigen fused to Lactadherin or a portion thereof comprising a functional C1 and/or C2 domain;
contacting said chimeric molecule with a lipid vesicle containing phosphatidyl serine or other lipids naturally contained in exosomes, to create functionalized lipid vesicles presenting said antigen at their surface, and
injecting said functionalized lipid vesicles or a portion thereof to said subject in the presence of lactadherin.

This invention also relates to a composition comprising a functionalized lipid vesicles as described above an lactadherin.

The lipid vesicle is preferably a liposome. The liposome may be produced according to conventional techniques, and, preferably, enriched for phosphatidyl serine or other lipids naturally contained in exosomes. The antigen can be any organic compound, such as a polypeptide, a nucleic acid, a lipid, a saccharide, a glycolipid, etc. The chimeric molecule may comprise the antigen either genetically (when the antigen is a polypeptide) or chemically coupled to Lactadherin, as described above.

In an other embodiment, the invention relates to a method of producing functionalized lipid vesicles, comprising:
Providing lipid vesicles containing phosphatidyl serine or other lipids naturally contained in exosomes, said vesicles carrying an activated Lactadherin comprising Lactadherin or a portion thereof comprising a functional C1 and/or C2 domain, activated by a reactive chemical group;
contacting said lipid vesicles with a compound that interacts with said reactive chemical group in order to produce functionalized lipid vesicles, and
optionally purifying said functionalized lipid vesicles.

As indicated above, the activated Lactadherin may be a portion of Lactadherin having a cysteine residue at one of its ends, thus creating reactive SH group. Such an activated Lactadherin may comprise, for instance, amino acids 1-230 of SEQ ID NO:7. Alternatively, the activated Lactadherin may be prepared by chemically adding to one of Lactadherin ends a reactive group such as a thiol, an ammo or a carboxyl group. The lipid vesicles carrying said activated Lactadherin can be an exosome or a synthetic vesicle for instance, such as a liposome. In this regard, in a particular embodiment, the invention relates to an exosome presenting an activated Lactadherin as described above. In an other embodiment, the invention relates to a liposome carrying an activated Lactadherin as described above. Such an exosomes or synthetic lipid vesicles may be produced as described above. The compound may be any organic molecule, such as a polypeptide, nucleic acid, lipid, glycolipid, saccharide, small molecule, drug (e.g., medicament), toxin, etc. Also, as indicated above, the lipid vesicle may be functionalized with various polypeptides, such as with an antigen, a targeting moiety and/or an adjuvant and/or Lactadherin Typical examples include a lipid vesicle comprising various polypeptides fused to Lactadherin or a functional C1 and/or C2 domain thereof, said polypeptides being selected from an antigen, a targeting polypeptide (e.g. a Fc fragment of an immunoglobulin) and an aduvant (e.g., a CD40 ligand, a cytokine, GM-CSF, etc.).

Genetic and DNA Vaccination

The present invention can also be used for direct DNA or genetic vaccination in vivo, using genetic constructs as disclosed above encoding chimeric antigen molecules.

Humoral or antibody response and cellular immune responses can also be generated against antigen upon genetic and DNA immunization. Chimeric sequences including full-length or partial cDNA encoding tumor or microbial antigens and the targeting polypeptide are prepared as described above. Viral, non viral vectors or DNA encoding these chimeric proteins can then be used directly to vaccinate individuals or animals. Genetic and DNA immunization has been shown to induce potent immune responses that lead to host protection against microbial infections and tumor regression (rev. Hasan et al J. Immunol. Methods 229, 1-22,1999). Recent findings suggest that cross-priming of antigen presenting cell (APC), i.e. the APC uptake of antigen exogenously produced by DNA-transfected non-APC, is a predominant mechanism for inducing strong immune responses upon genetic and DNA vaccination (Jae Ho Cho et al. J. Immunol. 167, 5549-5557, 2001). In addition, cell-associated cross-presentation of antigens has also been found to be much more efficient than cross-presentation of soluble antigens (Ming Li et al J. Immunol. 166, 6099-6103, 2001). Emanating from these findings, it is believed that an appropriate method of Ag transfer in vivo from DNA-transfected non-APC to APC is critical for the design of optimal genetic and DNA vaccines. In this regard, the genetic vaccination method according to the present invention offers the considerable advantage to directly address this criterion in that it leads to the production in vivo of antigens bound to exosomes that are then transferred to APC.

A further object of this invention thus resides in a method of delivering an antigen to a subject, comprising injecting to said subject a genetic construct encoding said antigen fused to a targeting polypeptide as described above, particularly to Lactadherin or a portion thereof comprising a functional C1 and/or C2 domain of Lactadherin.

An other object of this invention is a method of producing an immune response in a subject against a specific antigen, the method comprising injecting to said subject a genetic construct encoding said antigen fused to a targeting polypeptide as described above, particularly to Lactadherin or a portion thereof comprising a functional C1 and/or C2 domain of Lactadherin.

Genetic vaccination can be performed using a variety of viral vectors, such as vaccinia, pox virus, adenovirus, adeno associated virus, etc., non-viral vectors, such as DNA associated with various lipidic or peptidic compositions, or using pure (e.g., naked) DNA. Vaccination may be performed through various routes of injections, including intra muscular, intra-venous, subcutaneous or intra-dermal. Various vector delivery devices or techniques may be used for genetic vaccination, including gene gun or electroporation. Animals and individuals may also be immunized using cell lines transfected in vitro with the vectors. Cell lines selected for release of high number of exosomes would be particularly advantageous.

In a particular embodiment, the method comprises the direct injection of a naked DNA or RNA encoding the chimeric polypeptide. Naked means that the injected composition is free of any transfection facilitating agent. In a further preferred embodiment, the genetic construct is administered by intramuscular injection in a naked form, more preferably using a gene gun.

This method allows the cross-presentation of antigens in a non-soluble form via the exosome, whose function is to transfer antigens from cells in periphery to APC (cross-priming) (Wolfers et al Nature Medicine 7, 297-303, 2001). A schematic representation of the method is shown in FIG. 6. Immunization with a viral, non viral or naked DNA vector encoding chimeric proteins containing the C1/C2 domain of lactadherin leads to the expression of chimeric protein by various cells in vivo, including exosome-producing cells (step 1). The recombinant protein is then released in the extracellular milieu associated to exosomes (Step 2). Cross-priming of APC occurs when the chimeric protein-bearing exosomes binds to APC (Step 3).

In a particular embodiment, the cross-presentation of antigens to APC (step 3) may be further increased by administering, together with the chimeric protein-encoding genetic construct (e.g., DNA), a lactadherin-encoding genetic construct (e.g., DNA), since exosome binding to DC involves lactadherin. Alternatively, constructs may be prepared in which an antigen sequence is inserted within the full-length lactadherin sequence between the EGF domain and the C1C2 domain. Thereby, injection of a single construct produces antigens targeted to exosomes via the C1C2 domain of lactadherin and containing the receptor-binding domain of lactadherin that directs the specific delivery of exosome to DC.

Furthermore, in order to further increase the immune response, the genetic construct(s) encoding the antigen(s) and, optionally, Lactadherin, may be administered together with a genetic construct encoding an adjuvant, such as a factor or molecule that facilitates an immune reaction. Examples of such adjuvants include CD40Ligand, GM-CSF, cytokines, etc.

Moreover, in order to further increase the immune response, the genetic construct(s) encoding the antigen(s), Lactadherin and/or the adjuvant may be administered together with a genetic construct encoding a targeting polypeptide, such as a factor or molecule that directs exosomes to antigen-presenting cells. Examples of such targeting polypeptides include Fc fragments of immunoglobulins.

In this regard, in a particular embodiment, the method comprises injecting to the subject a genetic construct encoding the chimeric antigen and a genetic construct encoding Lactadherin or an accessory molecule fused to Lactadherin or a portion thereof comprising a functional C1 and/or C2 domain. The construct encoding Lactadherin or the chimeric accessory molecule may be injected simultaneously with the construct encoding the chimeric antigen, or separately. Where separate injections are performed, they may be made at about the same time or not. In particular, the construct encoding the chimeric antigen may be injected first, and then the construct encoding Lactadherin or the chimeric accessory molecule. It is preferred however that the various chimeric proteins be present simultaneously in vivo and be expressed by the same exosomes. In a particular embodiment, the proteins are expressed from genetic constructs contained in a single vector, such as a viral vector (e.g., a vaccinia virus).

In this regard, the invention also encompasses a composition comprising a genetic construct encoding an antigen fused to a targeting polypeptide, said targeting polypeptide being selected from (i) Lactadherin or a portion thereof comprising a functional C1 and/or C2 domain and (ii) targeting polypeptides identified by a method as described above, and (a) a genetic construct encoding an immune accessory molecule (e.g., an adjuvant or a cell targeting polypeptide) fused to a targeting polypeptide, said targeting polypeptide being selected from (i) Lactadherin or a portion thereof comprising a functional C1 and/or C2 domain and (ii) targeting polypeptides identified by a method as described above, and/or (b) a genetic construct encoding Lactadherin. The invention indeed allows to efficiently combine various functional molecules at the surface of exosomes, upon direct in vivo expression of such molecules in fusion with Lactadherin or portions thereof. This combined expression leads to an increased immune response, which mimicks antigenic particles or immune complexes.

Preferred examples are compositions comprising:

(a) a genetic construct encoding an antigen fused to a targeting polypeptide, said targeting polypeptide being selected from (i) Lactadherin or a portion thereof comprising a functional C1 and/or C2 domain and (ii) targeting polypeptides identified by a method as described above, (b) a genetic construct encoding an aduvant polypeptide fused to a targeting polypeptide, said targeting polypeptide being selected from (i) Lactadherin or a portion thereof comprising a functional C1 and/or C2 domain and (ii) targeting polypeptides identified by a method as described above, said adjuvant polypeptide being a cytokine, such as GM-CSF or IL-2, or CD40L, and/or (c) a genetic construct encoding an Fc fragment of an immunoglobulin fused to a targeting polypeptide, said targeting polypeptide being selected from (i) Lactadherin or a portion thereof comprising a functional C1 and/or C2 domain and (ii) targeting polypeptides identified by a method as described above, and/or (d) a genetic construct encoding Lactadherin.

As indicated above, the genetic construct may be any DNA or RNA molecule, typically a plasmid, viral vector, viral particle, naked DNA or any cell comprising the same. The various genetic constructs may be comprised within a single vector or in separate vectors or in any combination(s). The composition generally further comprises a pharmaceutically acceptable excipient or vehicle, such as a diluent, buffer, isotonic solution, etc. The composition may also include transfection facilitating agents, as described above.

Delivery of full-length or partial antigens to DC according to the present invention alleviates haplotypes restriction for vaccine usage. Also, delivery through a natural physiological pathway of antigen uptake by and transfer to DC will yield efficient processing of antigen and presentation of both class I and II epitopes. Hence, genetic and DNA vaccination with vector encoding tumor or microbial antigens targeted to exosomes contributes to improved genetic and DNA vaccines against cancer and infectious diseases.

A specific example of DNA vaccine composition against HV includes genetic constructs encoding an antigen selected from Reverse Transcriptase, gag, env, nef and tat polypeptides or portion thereof, fused to Lactadherin or a portion thereof comprising a functional C1 and/or C2 domain.

Furthermore, in addition to genetic vaccine, protein vaccines may also be used in a similar way. In this respect, recombinant chimeric antigens may be used in a purified form for administration into the patient. Following such an administration, chimeric antigens with C1 and/or C2 domain of Lactadherin will be loaded in vivo on the patient's own circulating exosomes, thereby producing an immune response.

An other object of this invention thus includes a method of producing an immune response in a subject against a specific antigen, the method comprising injecting to said subject a chimeric polypeptide comprising said antigen fused to a targeting polypeptide, said targeting polypeptide being selected from (i) Lactadherin or a portion thereof comprising a functional C1 and/or C2 domain and (ii) targeting polypeptides identified by a method as described above.

An other object of this invention is a method of delivering an antigen to a subject, comprising:
(a) Providing a chimeric genetic construct encoding said antigen fused to Lactadherin or a portion thereof comprising a functional C1 and/or C2 domain;
(b) Introducing said construct into exosome-producing cells to generate recombinant exosomes carrying said chimeric antigen at their surface,
(c) Collecting said recombinant exosomes and purifying the said chimeric antigen, and
(d) Injecting the purified chimeric antigens to said patient.

Recombinant Exosomes as Tools for Protein-Protein Interaction Studies

With the wealth of information provided by genome sequencing programs, genome-wide approaches for gene discovery and function assignment are being developed. Recombinant exosomes constitute a new technology to study protein-protein interaction and may allow high-throughput screening of libraries to identify each counterpart of a protein-protein interaction.

For such applications, proteins are expressed into two recombinant exosomes species with different protein profiles. The interaction of chimeric proteins from each recombinant exosome species with each other can be detected by standard ELISA-based assays using specific markers on the recombinant exosomes. This approach can be used to identify the counterparts of a known ligand or receptor.

In a particular embodiment, the invention thus resides in a method of selecting or identifying a ligand or binding partner of a polypeptide comprising:
(a) Providing a chimeric genetic construct encoding said polypeptide fused to a targeting polypeptide as described above, particularly to Lactadherin or a portion thereof comprising a functional C1 and/or C2 domain;
(b) Introducing said construct into exosome-producing cells to generate recombinant exosomes presenting said polypeptide at their surface,
(c) Contacting recombinant exosomes of (b) with a candidate compound and determining the ability of said candidate compound to bind said polypeptide on said exosome.

The candidate compound may be an isolated product, a mixture of products or a library of compounds. Examples of candidate compounds include, without limitation, small molecules (e.g., organic products) as well as libraries thereof, DNA libraries, protein libraries, libraries of antibodies (or fragments thereof), which may be displayed by phages or other presentation systems, etc. The candidate compounds may be tested in parallel or as complex mixtures.

Methods of determining the ability of a candidate compound to bind said polypeptide (or antigen) include, for instance, the isolation of the exosome and the immunization of a non-human mammal therewith. The generation of antibodies in said mammal indicates that a candidate molecule has complexed with the exosome and allows to identify said molecule.

This technique can be used to produce antibodies against a ligand of a molecule. For instance, a ligand of a receptor for which antibodies are needed is expressed according to this invention at the surface of a lipid vesicle. Such a vesicle is contacted with a preparation (e.g., a biological sample) containing said receptor. The exosomes are washed, purified and injected to a non-human-mammal.

Antibodies against the receptor can be isolated from said mammal. This strategy is very advantageous to produce antibodies against complex molecules, unstable molecules or even molecules that are not available in isolated form.

Purification or Recombinant Polypeptides

The invention also provides a method of producing a polypeptide from a functionalized exosome as described above. This method stems from the unexpected properties of lactadherin to selectively express or target polypeptides in exosomes. Hence, exosomes constitute an important source of Lactadherin or various chimeric polypeptides comprising a fragment of Lactadherin, from which these proteins can be recovered and/or purified. A particular advantage of this method is that the preparation of exosomes provides a rapid means to considerably enrich and concentrate proteins to be purified and allows to perform the purification of proteins from large-scale cell cultures with small sample volumes. In this method, Lactadherin or chimeric polypeptides comprising a functional C1 and/or C2 domain of Lactadherin can be produced, which are directly extracted from exosomes using standard biochemical approaches, including exosome lysis with detergent or salt and specific release of proteins with lipids or peptides, for instance. Alternatively, (native) proteins can be released directly from the exosome after proteolytic cleavage of the chimeric polypeptide, when a specific site has been inserted between the protein and the C1-C2 domain. Such sites are well characterized and include for instance a cleavage site for furin, enterokinase, factor X, etc. Extracted proteins can then be purified by standard chromatography approaches including anionic or hydrophobic chromatography and/or affinity chromatography on columns covalently linked to lectin, specific antibody, receptor or ligand and tag counterparts. This technique is also suited for purification of polypeptides fused to a targeting polypeptide identified as described above.

An other object of this invention thus resides in a method of producing a polypeptide comprising Lactadherin or a portion thereof, the method comprising:
a) Providing a genetic construct encoding said polypeptide;
b) Introducing said construct into exosome-producing cells to generate functionalized exosomes presenting said polypeptide at their surface,
c) Optionally collecting and/or purifying said functionalized exosomes, and
d) Recovering and/or purifying said polypeptide or a fragment thereof from said functionalized exosomes.

As indicated the polypeptide may be Lactadherin, such as wild-type Lactadherin or a fragment thereof. In this respect, the invention provides an efficient method of producing (and purifying) Lactadherin, comprising introducing a genetic encoding Lactadherin into exosome-producing cells to generate functionalized exosomes presenting said polypeptide at their surface, optionally collecting and/or purifying said functionalized exosomes, and recovering and/or purifying Lactadherin from said functionalized exosomes.

The polypeptide can be a chimeric polypeptide encoded by a chimeric genetic construct, which chimeric polypeptide comprises a polypeptide fused to a functional C1 and/or C2 domain of Lactadherin. In that case, the entire chimeric polypeptide may be recovered from the exosomes, or only a portion thereof, for instance the polypeptide released by separation from the C1 and/or C2 domain of Lactadherin. In this respect, a further object of this invention is a method of producing a polypeptide, comprising:
  a) Providing a genetic construct encoding said polypeptide fused to a targeting polypeptide, wherein said targeting polypeptide is selected from (i) Lactadherin or a portion thereof comprising a functional C1 and/or C2 domain and (ii) targeting polypeptides identified by the method a method as disclosed above, and wherein said polypeptide is fused to said targeting polypeptide through a spacer sequence that comprises a cleavage site;
  b) Introducing said construct into exosome-producing cells to generate functionalized exosomes presenting said polypeptide at their surface,
  c) Optionally collecting and/or purifying said functionalized exosomes,
  d) Treating said functionalized exosomes with an agent that cleaves said cleavage site, and
  e) Recovering and/or purifying said polypeptide.

The following examples are offered by way of illustration and not by way of limitation.

EXAMPLE 1

Human Lactadherin Expressed by Tumor Cell Lines is Found Almost Exclusively in Exosomes Human-derived tumor cells seeded at ~80% confluency in a 175 cm²-flask were cultured in complete media (RPMI 1640 supplemented with 2 mM L-glutamine, 100 U/ml Penicillin, 0.1 mg/ml Streptomycin, 1 mM Sodium Pyruvate and 10% fetal bovine serum (FBS)) for 4 days at 37° C. in a 5% $CO_2$ atmosphere. At day 4 of the culture, exosome lysates and cell lysates were prepared from each culture as follows:

The culture supernatants were harvested and successively spun at 200 g and filtered through a 0.2 µm filter to remove cell debris. The cleared supernatants were then spun at 4° C. for 90 min. under 100,000 g to pellet exosomes. The pellets were resuspended into 100 µl of ice-cold PBS. and the resulting fractions were retained as the exosome (E).

Tumor cells were detached from the culture dish following incubation at room temperature for 10 min. in 10 ml of Versene (Invitrogen). Cells were then pelleted by centrifugation at 4° C. for 10 min. under 200 g. The pellets were resuspended and lysed into 100 µl of ice-cold Lysis Buffer (LB) consisting of 50 mM Sodium phosphate pH 8.0, 300 mM sodium chloride, 10 mM imidazole and 0.5% Tween 20 and a cocktail of protease inhibitors (Sigma). The lysates were incubated for 10 min. on ice, were then cleared of insoluble materials by centrifugation for 10 min. at 4° C. under 10,000 g. The resulting supernatants were retained as the cell lysates (CL).

Eigth µl of SDS-PAGE Sample Buffer 5x (SB) was added to thirty-two PI of E and CL, incubated at 100° C. for 5 min. then analyzed by SDS-PAGE. Proteins on the gel were transferred to PVDF membranes following semi-dry electro-transfer and the presence of human lactadherin in the samples was established by immunodetection using a 1/2500 dilution of polyclonal antibody directed to the RGD motif of human Lactadherin (a gift from Dr. Sebastian Amigorena). Antibody bound to lactadherin was detected using a 1/5000 dilution of secondary anti-rabbit IgG antibody conjugated to horse-radish peroxidase (Jackson ImmunoResearch) and a colorimetic substrate (CN/DAB, Pierce).

CL and E samples were analysed in panel A and panel B of FIG. 1, respectively. In this assay, CL and E derived from the embryonic kidney cell 293 (lane 1), the melanoma cell FON-T1 (lane 2) and M10 (lane 3), the lung carcinoma cell NCI-N226 (lane 4) and NCI-H520 (lane 5), the melanoma cell FM3 (lane 6), the B lymphoblastoid cell Raji (lane 7) were tested.

Partially purified human Lactadherin from milk was used as positive control (lane 9) and E and CL from CHO, a hamster ovary cell line, were used as negative controls (lane 8 panel A and panel B, respectively).

Results: Lactadherin was detected in E (panel B) from 293 (lane 1), FON-T1 (lane 2), M10 (lane 3), NCI-H520 (lane 5) and FM3 (lane 6) whereas no specific band was detected in CL from the same cell lines (panel A). Lactadherin was not detected in E and CL from NCI-H226 (lane 4), Raji (lane 7) and the negative control CHO (lane 9).

Conclusion: Cell lines derived from various tumor tissues express lactadherin. The lactadherin expressed by these cell lines is found mainly in exosomes.

EXAMPLE 2

Recombinant Human Lactadherin is Expressed Almost Exclusively in Exosomes Produced by Transfected Cells and this Highly Specific Targeting is Encrypted in the C1/C2 Domain Two overlapping fragments of human Lactadherin cDNA were amplified from blood-derived total cDNA using primer pairs LTDNf15/LTDNr8 and LTDNf2/LTDNrl3, respectively (SEQ ID Nos: 1-4, respectively). LTDNf 15 and LTDNr13 were extended at their 5' end to include a Hind m and an Age I restriction site. The amplification of the 3' end of Lactadherin cDNA with LTDNf2/LTDNrl3 yielded multiple products, the longest of which corresponding to the known lactadherin cDNA (Lactlf, SEQ ID No:5). The sequence of the shorter form (Lactsf, SEQ ID No:6) lacks a stretch of 153 nucleotides resulting in a deletion of 51 amino acids in the C2 domain of Lactadherin The 5' end cDNA was digested with Hind III and EcoR I and both Lactlf and Lactsf cDNA were digested with Age I and EcoR I. The 5' end and 3' end cDNA were ligated together and into pcDNA6A-His (Invitrogen) that was precut with Hind III and Age I. The resulting plasmids (pcDNA6hLacts/His and pcDNA6hLactsf/His) encodes full-length recombinant human lactadherin fused to a $(His)_6$ tag (SEQ ID Nos: 7 and 8, respectively). They were transfected into 293 cells, a human embryonic kidney cell line (ATCC) using lipofectamine (Invitrogen). At day 4 of culture in complete media (see Example 1 for description of culture conditions and media), EL and CL were prepared from each culture as described in Example 1 (EL was prepared by resuspending exosomes in LB instead of PBS). In this experiment, the supernatants (S) obtained after the 100,000 g spin step to pellet exosomes was also retained. Ni-NTA agarose beads (Qiagen) were added to all the fractions to isolate His Tag-containing recombinant proteins only. Following a 2-hour incubation at 4° C. on a rocking platform, the beads were pelleted by centrifugation at 4° C. under 200 g. After three washes with LB adjusted to 20 mM imidazole, the beads were resuspended in 40 µl SB 1× and incubated at 100° C. for 5 min. The SB was collected and analyzed by SDS-PAGE and immunoblotting as described in FIG. 1.

CL, S and EL samples were analysed in panel A, B and panel C of FIG. 2, respectively. CL, S and EL derived from 293 transfected with pcDNA6hLactsf/His and pcDNA6hLactlf/His are shown in lane 1 and 2 of each panel, respectively.

Partially purified human Lactadherin from milk was used as positive control (lane 4) and CL, S and EL from 293 cells transfected with an empty pcDNA6 plasmid were used as negative controls (lane 3 of each panel).

Results: The long form of Lactadherin was detected in EL (lane 2, panel C) whereas only background levels were detected in S and CL derived from the same culture (lane 2, panel A and B, respectively). In contrast, the short form of Lactadherin with a 51-amino acid deletion in its C2 domain was detected exclusively in CL (lane 1, panel A) but neither in S nor in EL (lane 1, panel B and C, respectively).

Conclusion: Recombinant lactadherin expressed in 293 cells is almost exclusively found in exosomes. This highly specific targeting of recombinant Lactadherin to exosomes can be mediated by the C2 domain of this protein since a deletion in the C2 domain abrogates exosome targeting and may also affect the conformation of the C1 domain. Indeed, the recombinant short form of Lactadherin that lacks functional exosome targeting signal is found in a different cell compartment.

EXAMPLE 3

The Exosome Targeting Signal in the C2 Domain of Lactadherin is Conserved Across Various Mammalian Species The full-length cDNA of mouse lactadherin was amplified from a mouse Lactadherin cDNA template (a gift from Dr. Sebastian Amigorena) using primers LTDNf20 (SEQ ID No: 9) and LTDNr13 (SEQ ID No: 4). These primers were extended at their 5' end to include a Hind III and an Age I restriction site for primer LTDNf20 and LTDNr13, respectively. The product of amplification was digested with Hind III and Age I and ligated into pcDNA6A-His (Invitrogen) that was precut with the same enzymes. The resulting plasmid (pcDNA6 mLact/His) encodes recombinant mouse lactadherin fused to a $(His)_6$ tag (SEQ ID No: 10).

This plasmid and pcDNA6hLactlf/His (prepared as described in Example 2) were transfected into 293, CHO and WEHI (a mouse fibrosarcoma) cells and EL was prepared from each culture exactly as described in Example 2. Samples were prepared and Lactadherin expression was monitored as described in Example 1. EL from human 293 cells expressing mouse Lactadherin is shown in panel A, EL from mouse WEHI cells expressing human Lactadherin is shown in panel B and EL from hamster CHO cells expressing human Lactadherin is shown in panel C of FIG. 2. EL from cells transfected with Lactadherin-encoding plasmids are shown in lane 2 of each panel. EL from cells transfected with an empty pcDNA6 plasmid were used as negative controls (lane 1 of each panel). Partially purified human Lactadherin from milk was used as positive control (lane 3, panel C).

Results: Human Lactadherin expressed in mouse cells and hamster cells is found in exosomes produced by these cells (lane 2 of panel B and C, respectively). Mouse Lactadherin is also found in the exosomes produced by cells derived from a different species, i.e. human cells (lane 2, panel A).

Conclusion: The exosome targeting signal is conserved across several mammalian species.

EXAMPLE 4

Preparation of Chimeric Proteins

Chimeric proteins are generated by fusing the nucleotide sequences of a protein with that of the full-length or partial sequences of Lactadherin.

The full-length sequence of Lactadherin is generally fused upstream a protein sequence. Partial sequences of Lactadherin comprise the C1 domain only, the C2 domain only or both the C1 and the C2 domains and are generally fused downstream a protein sequence. Proteins that do not contain an intrinsic leader sequence can be inserted between the leader sequence and the C1/C2 domains of Lactadherin.

Chimeric proteins with different junctions are prepared by fusing the nucleotide sequence of a protein with the nucleotide sequence of a C domain and the matching C domain extended with at least 10 amino acids in its N-terminal extremity. Alternatively, chimeric proteins with different junctions are prepared using the C1 and the C2 domain of Lactadherin or using the C domains derived from two species. For instance, the chimeric proteins comprising the protein X and either human-derived C1, human-derived extended C1, human-derived C2 and mouse-derived C1 as fusion partners have different junctions.

Preparation of C1/C2 Fragments

The Lactadherin DNA fragments encoding C1, extended-C1, C2, extended-C2, C1/C2 and extended-C1/C2 domains were amplified using pcDNA6-hLaclf/His as template and the primer pairs LTDNf24 (SEQ ID No:13)/LTDNr26 (SEQ ID No:15), LTDNf22 (SEQ ID No:11)/LTDNr26, LTDNf25 (SEQ ID No:14)/LTDNr13, LTDNf23 (SEQ ID No:12)/LTDNr13, LTDNf24/LTDNr13 and LTDNf22/LTDNr13, respectively. The primer pairs LTDNf30 (SEQ ID No:16)/LTDNr26, LTDNf31 (SEQ ID No:17)/LTDNr26, LTDNf33 (SEQ ID No:19)/LTDNr13, LTDNf32 (SEQ ID No:18)/LTDNr13, LTDNf30/LTDNr13 and LTDNf31/LTDNr13, and the template pcDNA6-mLact/His is were used to amplify the matching C1/C2 fragments derived from mouse Lactadherin. All forward primers (LTDNf) are phosphorylated at their 5' end and all reverse primers (LTDNr) were extended at their 5' end to include an Age I restriction site. The products of amplification were digested with Age I before ligation with fusion partners (see below).

Preparation of Interleukin-2-C1/C2 Chimera

Full-length IL-2 cDNA was amplified from human activated-T cell cDNA template using primers IL2f1(SEQ ID No: 20) and IL2r2 (SEQ ID No: 21). IL2f1 was extended at its 5' end to include a Hind III restriction site whereas IL2r2 was phosphorylated at its 5' end. The product of amplification was digested with Hind III and ligated with each C1/C2 DNA fragment prepared above into pcDNA6A-His (Invitrogen) that was precut with Hind III and Age I. The blunt ligation between the phosphorylated 3' end of IL2 fragment and the phosphorylated 5' end of the C1/C2 fragments yield IL2-C1/C2 chimeric sequences. The 5' end Hind m site of IL2 fragment and 3' end Age I site of the C1/C2 fragments allow the insertion of the chimeric sequence into pcDNA6His and the resulting plasmids (pcDNA6-His/IL2-C1, IL2-extended-C1, IL2-C2, IL2-extended C2, IL2-C1/C2 and IL2-extended C1/C2) encode recombinant chimeric proteins fused to a (His)$_6$ tag (SEQ ID Nos: 22-27 for chimeric proteins containing human derived C1/C2 domains). In SEQ ID NO: 22-27, residues 1-153 correspond to the amino acid sequence of the hIL2 portion of the chimeric polypeptide, and the last C-terminal 8 amino acid residues of the chimeric polypeptide (TGHHHHHH) correspond to the His tag. The remaining residues correspond to lactadherin-derived sequence.

Expression of Biologically Active IL-2 in Exosomes

The plasmids described above and encoding SEQ ID 22-27 were transfected into WEHI cells. Fractions EL, CL and S were prepared as described in Example 1. Expression of recombinant protein was assessed by western blot as described in Example 1 except that the detecting antibody used here was a rabbit anti-IL2 antibody.

CL, S and EL samples were analysed in panel A, B and panel C of FIG. 4, respectively. CL, S and EL derived from cells transfected with pcDNA6IL2-extendedC1/His, pcDNA6IL2-extendedC2/His, pcDNA6IL2-extendedC1/C2/His, pcDNA6IL2-C1/His, pcDNA6IL2-C2/His, and pcDNA6IL2-C1/C2/His are shown in lane 1 to 6 of each panel, respectively.

Recombinant IL2 was used as positive control (lane 8 of panel C) and CL, S and EL from untansfected cells were used as negative controls (lane 7 of each panel).

Results: All chimeric IL2-C1/C2 genes prepared expressed recombinant proteins that react with an anti-IL2 antibody (lane 1 to 6, panel C). In addition, these proteins were almost exclusively found in EL as only low or background expression was detected in S and EL (lane 1 to 6, panel A and B, respectively). In order to determine whether the IL2-C1/C2 chimeric proteins detected in exosome display IL2 activities, CTLL-2, an IL2-dependent cell line was incubated with either recombinant exosomes bearing IL2-C1/C2 chimeric proteins or exosomes from untransfected cells. We found that cells incubated with recombinant exosomes incorporated 3H-thymidine whereas cells incubated with exosomes from untransfected cells did not (data not shown).

Conclusion: The fusion of IL2 with the C1/C2 domain of Lactadherin results in the expression of IL2 in exosomes supporting that these domains are able to specifically direct expression of an antigen to exosomes. Both C1 and C2 domain are also functional individually. The chimeric proteins containing single C domains were produced in larger amounts than the chimeric proteins containing both C1 and C2. Finally, the fusion yielded a chimeric protein containing biologically active IL2 supporting that IL2 is maintained in a native conformation. Therefore, targeting of proteins to exosomes using the C1/C2 domain of Lactadherin may indeed results in the production of recombinant exosomes with new biological functions.

EXAMPLE 5

Purification of Recombinant Human Lactadherin

Plasmid pcDNA6hLactlf/His encoding the full-length recombinant human lactadherin fused to a (His)$_6$ tag (SEQ ID No: 7) was prepared as described in Example 2. This plasmid was transfected into CHO cells, a hamster ovarian cell line (ATCC) using lipofectamine (Invitrogen). At day 1 of culture in complete media (CHO-SFM supplemented with 2 mM 1-glutamine, 100 U/ml Penicillin, 0.1 mg/ml Streptomycin and 2% fetal bovine serum (FBS)) at 37° C. in a 5% CO$_2$ atmosphere, stably transfected cells were selected in media supplemented with 2 μg/ml Blasticidin. After 4 days of culture, stable clones were isolated by the limiting dilution technique. Clones producing large amounts of Lactadherin were selected by western blot analysis of recombinant Lactadherin expressed in exosomes as described in example 2. The clone CHO-3.2 was expanded into 1-liter spinner flask and grown in complete media without FBS for large-scale production of Lactadherin Seven-day cell culture supernatant was transferred into 250 ml centrifuge bottles and spun 5 min at 2000 rpm to pellet cells. The supernatant was then filtered through 0.2 μm filter flask and concentrated to 100 ml using a fiber cartridge with a 500K size cut-off. Concentrated supernatant was then spun under 100,000×g for 1 hour 15 min at 4° C. The pellet containing exosome was resuspended in 1 ml MLBII (50 mM NaPO4 pH 8/300 mM NaCY 10 mM imidazole/0.5% Tween) and transferred into a tube containing 2 mls Ni-NTA slurry (prespun to remove EtOH). After an incubation of 2-3 hours at 4° C. on a shaker, the sample was poured into a BioRad column and allowed to settle at 4° C. The column was washed with 10 mls MWBI (50 mM NaPO4 pH 8/300 mM NaCl/20 mM imidazole/0.05% Tween then with 20 mls MWBII (50 mM NaPO4 pH 8/500 mM NaCl/20 mM imidazole). Proteins bound to the column were eluted with 8 mls MEBII (50 mM NaPO4 pH 8/300 mM NaCl/250 mM imidazole). Eluted proteins were concentrated and buffer was exchanged to PBS pH 7.4 using a Millipore Ultrafree-4 10,000 MWCO device. The protein sample was aliquoted and stored at −20° C. Purity was analyzed by Coomassie staining of an SDS-PAGE. FIG. 5 shows the analysis of two preparations of recombinant Lactadherin (A and B, respectively) pre- and post-concentration (lane 1; 50 μl and lane 2; 1 μg, respectively).

In conclusion, the procedure described herein yields highly purified recombinant Lactadherin.

EXAMPLE 6

Screening of Exosomal Proteins for the Targeting of Antigens to Exosomes

The presence of exosome targeting domains on other proteins and their usage to target antigens to exosomes was evaluated with MelanA/MART1, CD40L and CD81.

In a first set of experiments, the cDNA encoding MelanA/MART1, CD40L and CD81 were amplified from FM3 cell cDNA (MelanA/MART1) and mouse spleen cell cDNA (Clonetech, CD40L, CD81), using specific primers. The primers were extended at their 5' end to include a restriction site, for cloning purposes. The products of amplification were digested with the restriction enzymes and ligated separately into pcDNA6A-His (Invitrogen) that was precut with the matching enzymes. The resulting plasmids (pcDNA6-MART1, pcDNA6-CD40L and pcDNA6-CD81, respectively) encode recombinant MelanA/MART1 (SEQ ID No: 28), CD40L (SEQ ID No: 29) and CD81 (SEQ ID No: 30). Recombinant MelanA/MART1 and CD81 are fused to a Myc tag followed by a His tag that were provided in the vector. More specifically, in SEQ ID NO: 28, residues 1-118 correspond to MelanA/MART1, residues 120-129 correspond to a Myc tag and residues 133-140 correspond to a His tag. Similarly, in SEQ ID NO: 30, residues 1-236 correspond to CD81, residues 238-247 correspond to a Myc tag and residues 251-258 correspond to a His tag.

EL4 and 293F cells were transfected by electroporation (220 V, 950 μF for EL4 and 400 V, 200 μF for 293F) with plasmids encoding SEQ ID Nos: 28 to 30, respectively. Fractions EL and CL were prepared as in Example 1 except that exosome and cell pellets were directly resuspended in SB 1× for SDS-PAGE. Expression of recombinant protein was assessed by Western blot also as described in Example 1 except that the detecting antibody used here was a mouse anti-Myc tag antibody for MelanA/MART1 and CD81 and an anti-CD40L antibody for CD40L. MelanA/MART1, CD40L and CD81 samples were analysed in panel A, B and C of FIG. 7, respectively. EL of transfected and untransfected cells and CL of transfected and untansfected cells are shown in lanes 1 to 4 of each panel, respectively.

In a second set of experiments, the cDNA encoding the seven-transmembrane receptor CCR7 was amplified from activated dendritic cells using specific primers. Both primers were extended at their 5' end to include an Age I restriction site. The amplified product was digested with Age I and ligated into the plasmid encoding Seq ID No: 29 precut with Age I. Age I-digested product was also ligated into a plasmid encoding a truncated form of CD81 (pcDNA6-CD81E, SEQ ID No: 31) which was prepared as SEQ ID No: 30 using a particular primer. The truncation of the C-terminal transmembrane region of CD81 in SEQ ID No: 31 was required to maintain the proper orientation of CCR7 in lipid bilayer of cellular membrane. In SEQ ID No: 31, residues 1-200 correspond to CD81E, residues 202-211 correspond to a Myc tag and residues 215-222 correspond to a His tag. Ligations in plasmids encoding SEQ ID Nos: 28 and 31 yielded the insertion of CCR7 cDNA between the Myc and His Tag of the plasmid recipient. Plasmids with the CCR7 insert in 5' to 3' orientation were selected by PCR screening. The selected plasmids (pcDNA6-MARTlI/CCR7 and pcDNA6-CD81E/CCR7) encode recombinant chimeric proteins fused to a His tag (SEQ ID Nos: 32 and 33, respectively). In SEQ ID No: 32, residues 1-118 correspond to MelanA/MART1, residues 120-129 correspond to a Myc tag, residues 135-488 correspond to CCR7 and residues 489496 correspond to a His tag. In SEQ ID No: 33, residues 1-200 correspond to CD81E, residues 202-211 correspond to a Myc tag, residues 217-570 correspond to CCR7 and residues 571-578 correspond to a His tag.

EL4 cells were transfected by electroporation with plasmids encoding SEQ ID Nos: 32 and 33 and EL and CL fractions were prepared as described above. Expression of recombinant protein was assessed by Western blot also as described above. EL and CL samples were analysed in panel A and B of FIG. 8, respectively. Samples derived from cells transfected with pcDNA6-MART1/CCR7, pcDNA6-CD81E/CCR7 and untransfected cells are shown in lane 1 to 3 of each panel, respectively.

Results: Recombinant MelanA/MART1 (Panel A, FIG. 7), CD40L (Panel B, FIG. 7) and CD81 (Panel C, FIG. 7) were detected in exosomes and also in cell lysates of transfected cells (Lane 1 and 3 of each panel, respectively). Noticeably, the expected long form of CD40L (transmembrane form) was detected in CL (Lane 3 panel B) whereas mainly the short form (soluble form) was detected in exosomes (Lane 1 panel B). Smaller size products most likely due to uncontrolled proteolysis of CD81 in cell lysates were detected in Lane 3, panel B. Recombinant chimeric MelanA/MART1-CCR7 was detected in exosomes but not in cell lysates of transfected cells (Lane 1, Panel A and B, respectively, FIG. 8). Using FACS analysis, we verified that a control construct encoding CCR7 alone yielded as expected a recombinant receptor that could be detected on the cell surface but not on exosomes of transfected cells (data not shown). Finally, the plasmid encoding the chimeric protein CD81E/CCR7 did not yield detectable levels of protein in any of the fractions tested (Lane 2, Panel A and B, FIG. 8). No protein was detected in the fractions derived from untransfected cells (Lane 2 and 4, Panel A to C, FIG. 7 and Lane 3, Panel A and B, FIG. 8).

Conclusion: As demonstrated using lactadherin, other exosomal protein can be identified and used to target antigens and notably receptors. Indeed, MelanA/MART1 was identified as being mainly expressed in exosomes and its fusion to a seven-transmembrane receptor, CCR7, triggers the expression of CCR7 on exosomes. This phenomenon is fusion-partner specific since CCR7 could not be detected when using another exosomal protein, i.e. CD81E, as fusion-partner. Therefore, the screening of exosomal proteins for their ability to target other protein to exosomes will result in the identification of novel candidates like MelanA/MART1 that can be used for the same applications using the C1C2 domain of lactadherin. It should be noted that despite the fact that no CD81E/CCR7 was detected, CD81 may still be suitable for the targeting of other antigen than CCR7 to exosomes.

EXAMPLE 7

Immunogenicity of Recombinant Proteins Displayed on Exosomes

Mouse exosomes derived from WEHI cells transfected with pcDNA6hLactlf/His were prepared as described in Example 3. Purified human recombinant Lactadherin was prepared as described in Example 5. Nine Balb/C mice were arranged in three immunization groups of three mice. Each mouse was immunized intraperiteonally with either ~20 ng recombinant human lactadherin in PBS (Group 1), ~20 ng recombinant human lactadherin in a 1:1 PBS/Complete Freund's Adjuvant mix (Group 2) or recombinant WEHI exosomes containing ~20 ng human lactadherin in PBS (Group 3). Animals received a boost two weeks after the first injection with the same samples except group 2 where the antigen was resuspended in a 1:1 PBS/Incomplete Freund's Adjuvant mix. Animals were bled after the second immunization and tested for anti-human lactadherin antibody by ELISA. For the ELISA, 50 ng human Lactadherin in PBS was coated the wells of a microtitration plate for one hour at 37° C. Blocking buffer containing 0.05% Tween-20 and 6% Non-Fat Dry Milk in PBS was added to the wells for one hour at room temperature (RT) to saturate the remaining free binding sites. Wells were then incubated for one hour at RT with serum of immunized mice at a dilution 1/1000 in Blocking buffer. After washing the wells three times with Blocking buffer, bound antibodies were detected using a 1/10000 dilution of secondary anti-mouse IgG conjugated to horse-radish peroxidase (Jackson ImmunoResearch) and a chemiluminescent substrate (Amersham). The results are shown in FIG. 9.

Results: Anti-lactadherin antibodies were detected in the serum of mice immunized with lactadherin-containing exosomes whereas no antibody response was generated when lactadherin was given alone or as an emulsion in Freund's Adjuvant. No antibody was detected when using Freund's adjuvant even after four injections of the inoculum whereas the titer of antibody in serum of mice receiving lactadherin-bearing exosomes increased with subsequent injections (data not shown).

Conclusion: Exosomes bearing antigens act as powerful immunoges in the absence of any adjuvant and can induce an antibody response using very low amounts of antigens, amounts at which a classical and already potent adjuvant such as Freund's Adjuvant is inefficient.

REFERENCES

1. Couto, J. R., Taylor, M. R., Godwin, S. G., Ceriani, R. L. and Peterson, J. A. Cloning and sequence analysis of human breast epithelial antigen BA46 reveals an RGD cell adhesion sequence presented on an epidermal growth factor-like domain. DNA CELL BIOL 15, 281-6,1996.
2. Andersen, M. H., Berglund, L., Rasmussen, J. T. and Petersen, T. E. Bovine PAS-6/7 binds alpha v beta 5 integrins and anionic phospholipids through two domains. Biochemistry 36, 5441-6., 1997
3. Andersen, M. H., Graversen, H., Fedosov, S. N., Petersen, T. E. and Rasmnussen, J. T. Functional analyses of two cellular binding domains of bovine lactadherin. Biochemistry 39, 6200-6., 2000
4. Garin, J., Diez, R., Kieffer, S., Dermine, J. F., Duclos, S., Gagnon, E., Sadoul, R., Rondeau, C. and Desjardins, M. The phagosome proteome: insight into phagosome functions. J Cell Biol 152, 165-80., 2001
5. Thery, C., Regnault, A., Garin, J., Wolfers, J., Zitvogel, L., Ricciardi-Castagnoli, P., Raposo, G. and Amigorena, S. Molecular characterization of dendritic cell-derived exosomes. Selective accumulation of the heat shock protein hsc73. J Cell Biol 147, 599-610, 1999
6. Thery, C., Boussac, M., Veron, P., Ricciardi-Castagnoli, P., Raposo, G., Garin, J. and Amigorena, S. Proteomic analysis of dendritic cell-derived exosomes: a secreted subcellular compartment distinct from apoptotic vesicles. J Immunol 166, 7309-18., 2001
7. Wolfers, J., Lozier, A., Raposo, G., Regnault, A., Thery, C., Masurier, C., Flament, C., Pouzieux, S., Faure, F., Tursz, T., Angevin, E., Amigorena, S. and Zitvogel, L. Tumor-derived exosomes are a source of shared tumor rejection antigens for CTL cross-priming. Nat Med 7,297-303., 2001
8. Zitvogel, L., Regnault, A., Lozier, A., Wolfers, J., Flament, C., Tenza, D., Ricciardi-Castagnoli, P., Raposo, G. and Amigorena, S. Eradication of established murine tumors using a novel cell-free vaccine: dendritic cell-derived exosomes. Nat Med 4, 594-600, 1998
9. Thery C., Zitvogel L. and Amigorena S. Exosomes: Composition, Biogenesis and Function. Nature review 2 (2002) 569
10. K. Denzer, M. van Eijk, M. J. Kleijmeer, E. Jakobson, C. de Groot and H. J. Geuze. Follicular Dendritic Cells carry MHC Class II-Expressing Microvesicles at Their Surface. J. Immunol. 165 (2000), 1259-1265

We claim:

1. A chimeric genetic construct, wherein said construct encodes a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide being a partial human lactadherin sequence selected from the group consisting of the C1 domain of the human lactadherin sequence consisting essentially of amino acid residues 69-225 of SEQ ID NO:7, the C2 domain of the human lactadherin sequence consisting essentially of amino acid residues 229-387 of SEQ ID NO:7, and the C1 and C2 domain of the human lactadherin consisting essentially of amino acid residues 69-387 of SEQ ID NO:7, wherein said targeting polypeptide selectively targets said polypeptide of interest to exosomes.

2. A chimeric genetic construct of claim 1, wherein said construct encodes a polypeptide selected from SEQ ID NO: 22, 24 and 26 or a fragment thereof devoid of the 8 C-terminal amino acid residues.

3. A vector comprising a chimeric genetic construct of claim 1.

4. A recombinant cell comprising a chimeric genetic construct of claim 1.

5. A method of selecting or identifying a ligand or binding partner of a polypeptide comprising:
   (a) Providing a chimeric genetic construct of claim 1, wherein said polypeptide of interest is said polypeptide;
   (b) Introducing said construct into exosome-producing cells to generate recombinant exosomes presenting said polypeptide at their surface,
   (c) Contacting recombinant exosomes of (b) with a candidate compound and determining the ability of said candidate compound to bind said polypeptide on said exosome.

6. A method of delivering an antigen to a subject comprising:
   (a) Providing a chimeric genetic construct of claim 1, wherein said polypeptide of interest is said antigen;
   (b) Introducing said construct into exosome-producing cells to generate recombinant exosomes carrying said antigen at their surface,
   (c) Collecting said recombinant exosomes and optionally contacting said recombinant exosome ex vivo with dentritic cells from said subject and,
   (d) injecting to said subject said recombinant exosomes or said contacted dendritic cells or exosomes produced by said contacted dendritic cells.

7. The method of claim 6, wherein the antigen is a tumor, a viral or a microbial antigen.

8. A method of delivering an antigen to a subject, comprising injecting to said subject a genetic construct of claim 1, wherein said polypeptide of interest is said antigen.

9. A method of producing an immune response in a subject against a specific antigen, the method comprising injecting to said subject a genetic construct of claim 1, wherein said polypeptide of interest is said antigen, the expression of said genetic construct causing production of an immune response in the subject against said antigen.

10. The method of claim 8, wherein said genetic construct is a naked DNA or RNA and wherein said genetic construct is administered in naked form by direct intramuscular injection.

11. The method of claim 8, further comprising injecting to the subject a further genetic construct encoding an accessory molecule fused to Lactadherin or a portion thereof comprising a functional C1 and/or C2 domain.

12. The method of claim 9, wherein said genetic construct is injected in naked form with a gene gun.

13. The method of claim 11, wherein said accessory molecule is an adjuvant.

14. The method of claim 11, wherein said accessory molecule is a cell targeting polypeptide.

15. The method of claim 13, wherein the adjuvant is a polypeptide cytokine, such as GM-CSF and IL-2 or CD40L.

16. The method of claim 8, wherein the genetic construct is administered in a virus.

17. The method of claim 8, wherein the genetic construct is administered in a plasmid.

18. The method of claim 8, wherein the genetic construct is administered by electroporation.

19. A composition comprising a genetic construct of claim 1, wherein said polypeptide of interest is an antigen, and a genetic construct encoding an immune accessory molecule fused to a second targeting polypeptide, said second targeting polypeptide being selected from Lactadherin or a portion thereof comprising a functional C1 and/or C2 domain.

20. A method of producing an exosome expressing a selected trans-membrane polypeptide, the method comprising:
providing a genetic construct of claim 1, wherein the polypeptide of interest is a selected trans-membrane polypeptide,
expressing the genetic construct into exosome-producing cells, and
producing and isolating exosomes from said modified cells.

21. A method of producing an exosome expressing a GPCR or a portion thereof comprising at least one trans-membrane domain, the method comprising:
providing a genetic construct of claim 1, wherein said polypeptide of interest is a G-Protein Coupled Receptor or portion thereof,
expressing the genetic construct into exosome-producing cells, and
producing and isolating exosomes from said modified cells which express the GPCR or portion thereof.

22. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide is the C1 domain of human lactadherin, and said C1 domain is amino acid residues 69-225 of SEQ ID NO:7.

23. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide is the C2 domain of human lactadherin, and said C2 domain is amino acid residues 229-387 of SEQ ID NO:7.

24. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide is the C1 and C2 domain of human lactadherin, and said C1 and C2 domain is amino acid residues 69-387 of SEQ ID NO:7.

25. A chimeric genetic construct, wherein said construct encodes a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide being a partial murine lactadherin sequence selected from the group consisting of the C1 domain of the murine lactadherin consisting essentially of amino acid residues 111-266 of SEQ ID NO: 10, the C2 domain of the murine lactadherin consisting essentially of amino acid residues 271-426 of SEQ ID NO: 10, and the C1 and C2 domain of the murine lactadherin consisting essentially of amino acid residues 111-426 of SEQ ID NO: 10, wherein said targeting polypeptide selectively targets said polypeptide of interest to exosomes.

26. A vector comprising a chimeric genetic construct of claim 25.

27. A recombinant cell comprising a chimeric genetic construct of claim 25.

28. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide being the C1 domain of murine lactadherin corresponding to amino acid residues 111-266 of SEQ ID NO: 10.

29. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide being the C2 domain of murine lactadherin corresponding to amino acid residues 271-426 of SEQ ID NO: 10.

30. A chimeric genetic construct, wherein said construct encodes a fusion polypeptide comprising a polypeptide of interest fused to a targeting polypeptide, said polypeptide of interest being selected from an antigen, a cytokine, a ligand, a receptor, an immunoglobulin, a marker polypeptide, an enzyme and an ionic channel, or a portion thereof, and said targeting polypeptide being the C1 and C2 domain of murine lactadherin corresponding to amino acid residues 111-426 of SEQ ID NO: 10.

31. A method of targeting a polypeptide of interest to exosomes, comprising:
Providing a chimeric genetic construct of claim 1 or claim 25; and
Introducing said construct into exosome-producing cells in vivo or ex vivo, to generate recombinant exosomes to which said polypeptide is targeted.

32. A method of claim 31 for selectively expressing a polypeptide at the surface of exosomes, further comprising:
Collecting recombinant exosomes which carry at their surface a polypeptide encoded by said chimeric genetic construct.

33. The method of claim 31, wherein the lactadherin has an amino acid sequence comprising SEQ ID NO: 7, 8, 10.

34. The method of claim 33, wherein the lactadherin has an amino acid sequence consisting essentially of amino acid residues 69-225 of SEQ ID NO:7, amino acid residues 229-387 of SEQ ID NO:7, amino acid residues 69-387 of SEQ ID NO: 7, amino acid residues 111-266 of SEQ ID NO:10, amino acid residues 109-266 of SEQ. ID NO:10, amino acid residues 271-426 of SEQ ID NO:10, amino acid residues 111-426 of SEQ ID NO:10 or amino acid residues 109-426 of SEQ ID NO:10.

35. The method of claim 32, wherein the chimeric genetic construct comprises a leader signal sequence to favor secretion of the encoded chimeric polypeptide into the endoplasmic reticulum of said exosome-producing cells.

36. The method of claim 32, wherein said polypeptide is fused upstream, downstream or at any internal domain junction of the targeting polypeptide.

37. The method of claim 32, wherein several distinct chimeric genetic constructs encoding distinct polypeptides are introduced into said exosome-producing cells.

38. The method of claim 32, wherein said exosome-producing cells are mammalian cells.

* * * * *

```
                         SEQUENCE LISTING

<160> NUMBER OF SEQ ID NOS: 33

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer
      LTDNf15

<400> SEQUENCE: 1
tataagctta gcatgccgcg cccccgcctg                                          30

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer
      LTDNr8

<400> SEQUENCE: 2
ggattggcgc atccgttcag c                                                   21

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer
      LTDNf2

<400> SEQUENCE: 3
gccctggata tctgttcc                                                       18

<210> SEQ ID NO 4
<211> LENGTH: 30
<212> TYPE: DNA
```

```
<213> ORGANISM: Artificial Sequence
<220> FEATURE:
<223> OTHER INFORMATION: Description of Artificial Sequence: Primer
      LTDNr13

<400> SEQUENCE: 4
ataaccggta cagcccagca gctccaggcg                                         30

<210> SEQ ID NO 5
<211> LENGTH: 1164
<212> TYPE: DNA
<213> ORGANISM: Artificial Sequence
<220> FEATURE:
<223> OTHER INFORMATION: Description of Artificial Sequence:Lact1f

<400> SEQUENCE: 5
atgccgcgcc ccgcctgctg gccgcgctg tgcggcgcgc tgctctgcgc ccccagcctc         60
ctcgtcgccc tggatatctg ttccaaaaac ccctgccaca acggtggttt atgcgaggag       120
atttcccaag aagtgcgagg agatgtcttc ccctcgtaca cctgcacgtg ccttaagggc       180
tacgcgggca accactgtga gacgaaatgt gtcgagccac tgggcatgga gaatgggaac       240
attgccaact cacagatcgc cgcctcatct gtgcgtgtga ccttcttggg tttgcagcat       300
tgggtcccgg agctggcccg cctgaaccgc gcaggcatgg tcaatgcctg gacacccagc       360
agcaatgacg ataaccctg gatccaggtg aacctgctgc ggaggatgtg ggtaacaggt        420
gtggtgacgc agggtgccag ccgcttggcc agtcatgagt acctgaaggc cttcaaggtg       480
gcctacagcc ttaatggaca cgaattcgat ttcatccatg atgttaataa aaaacacaag       540
gagtttgtgg gtaactggaa caaaaacgcg gtgcatgtca acctgtttga ccccctgtg        600 gaggctcagt acgtgagatt gtaccccacg agctgccaca cggcctgcac tctgcgcttt       660
gagctactgg gctgtgagct gaacggatgc gccaatcccc tgggcctgaa gaataacagc       720
atccctgaca gcagatcac ggcctccagc agctacaaga cctggggctt gcatctcttc        780
agctggaacc cctcctatgc acggctggac aagcagggca acttcaacgc ctgggttgcg       840
gggagctacg gtaacgatca gtggctgcag gtggacctgg gctcctcgaa ggaggtgaca       900
ggcatcatca cccagggggc ccgtaacttt ggctctgtcc agtttgtggc atcctacaag       960
gttgcctaca gtaatgacag tgcgaactgg actgagtacc aggaccccag gactggcagc      1020
agtaagatct tccctggcaa ctgggacaac cactcccaca gaagaacttt gtttgagacg      1080
cccatcctgg ctcgctatgt gcgcatcctg cctgtagcct ggcacaaccg catcgccctg      1140
cgcctggagc tgctgggctg ttag                                             1164

<210> SEQ ID NO 6
<211> LENGTH: 1008
<212> TYPE: DNA
<213> ORGANISM: Artificial Sequence
<220> FEATURE:
<223> OTHER INFORMATION: Description of Artificial Sequence:Lactsf

<400> SEQUENCE: 6
atgccgcgcc ccgcctgctg gccgcgctg tgcggcgcgc tgctctgcgc ccccagcctc         60
ctcgtcgccc tggatatctg ttccaaaaac ccctgccaca acggtggttt atgcgaggag       120
atttcccaag aagtgcgagg agatgtcttc ccctcgtaca cctgcacgtg ccttaagggc       180
tacgcgggca accactgtga gacgaaatgt gtcgagccac tgggcatgga gaatgggaac       240
attgccaact cacagatcgc cgcctcatct gtgcgtgtga ccttcttggg tttgcagcat       300
```

-continued

```
tgggtcccgg agctggcccg cctgaaccgc gcaggcatgg tcaatgcctg gacacccagc    360
agcaatgacg ataaccccctg gatccaggtg aacctgctgg ggaggatgtg ggtaacaggt    420
gtggtgacgc agggtgccag ccgcttggcc agtcatgagt acctgaaggc cttcaaggtg    480
gcctacagcc ttaatggaca cgaattcgat ttcatccatg atgttaataa aaaacacaag    540
gagtttgtgg gtaactggaa caaaaacgcg gtgcatgtca acctgtttga gacccctgtg    600
gaggctcagt acgtgagatt gtaccccacg agctgccaca cggcctgcac tctgcgcttt    660
gagctactgg gctgtgagct gaacggatgc gccaatcccc tgggcctgaa gaataacagc    720
atccctgaca agcagatcac ggcctccagc agctacaaga cctggggctt gcatctcttc    780
agctggaacc cctcctatgc acggctggac aagcagggca acttcaacgc ctgggttgcg    840
gggagctacg gtaacgatca gtggctgcag atcttccctg caactgggga caaccactcc    900
cacaagaaga acttgtttga gacgcccatc ctggctcgct atgtgcgcat cctgcctgta    960
gcctggcaca accgcatcgc cctgcgcctg gagctgctgg gctgttag              1008
```

<210> SEQ ID NO 7
<211> LENGTH: 395
<212> TYPE: PRT
<213> ORGANISM: Artificial Sequence
<220> FEATURE:
<223> OTHER INFORMATION: Description of Artificial Sequence: hLACTLF/His

<400> SEQUENCE: 7

```
Met Pro Arg Pro Arg Leu Leu Ala Ala Leu Cys Gly Ala Leu Leu Cys
 1               5                  10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
        50                  55                  60

His Cys Glu Thr Lys Cys Val Glu Pro Leu Gly Met Glu Asn Gly Asn
 65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240
```

```
Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
                275                 280                 285

Leu Gln Val Asp Leu Gly Ser Ser Lys Glu Val Thr Gly Ile Ile Thr
290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
                340                 345                 350

His Lys Lys Asn Leu Phe Glu Thr Pro Ile Leu Ala Arg Tyr Val Arg
                355                 360                 365

Ile Leu Pro Val Ala Trp His Asn Arg Ile Ala Leu Arg Leu Glu Leu
370                 375                 380

Leu Gly Cys Thr Gly His His His His His His
385                 390                 395

<210> SEQ ID NO 8
<211> LENGTH: 343
<212> TYPE: PRT
<213> ORGANISM: Artificial Sequence
<220> FEATURE:
<223> OTHER INFORMATION: Description of Artificial Sequence: hLACTSF/His

<400> SEQUENCE: 8

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205
```

```
Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
                260                 265                 270

Gly Asn Phe Asn Ala Trp Val Ala Gly Ser Tyr Gly Asn Asp Gln Trp
                275                 280                 285

Leu Gln Ile Phe Pro Gly Asn Trp Asp Asn His Ser His Lys Lys Asn
    290                 295                 300

Leu Phe Glu Thr Pro Ile Leu Ala Arg Tyr Val Arg Ile Leu Pro Val
305                 310                 315                 320

Ala Trp His Asn Arg Ile Ala Leu Arg Leu Glu Leu Leu Gly Cys Thr
                325                 330                 335

Gly His His His His His His
                340

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer
      LTDNf20

<400> SEQUENCE: 9
ataaagctta gcatgcaggt ctcccgtgtg                                         30

<210> SEQ ID NO 10
<211> LENGTH: 434
<212> TYPE: PRT
<213> ORGANISM: Artificial Sequence
<220> FEATURE:
<223> OTHER INFORMATION: Description of Artificial Sequence: mLACT/His

<400> SEQUENCE: 10

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
            35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Gly Cys Ser
                100                 105                 110

Thr Gln Leu Gly Met Glu Gly Gly Ala Ile Ala Asp Ser Gln Ile Ser
            115                 120                 125

Ala Ser Tyr Val Tyr Met Gly Phe Met Gly Leu Gln Arg Trp Gly Pro
    130                 135                 140

Glu Leu Ala Arg Leu Tyr Arg Thr Gly Ile Val Asn Ala Trp His Ala
145                 150                 155                 160
```

-continued

```
Ser Asn Tyr Asp Ser Lys Pro Trp Ile Gln Val Asn Leu Leu Arg Lys
            165                 170                 175

Met Arg Val Ser Gly Val Met Thr Gln Gly Ala Ser Arg Ala Gly Arg
        180                 185                 190

Ala Glu Tyr Leu Lys Thr Phe Lys Val Ala Tyr Ser Leu Asp Gly Arg
    195                 200                 205

Lys Phe Glu Phe Ile Gln Asp Glu Ser Gly Gly Asp Lys Glu Phe Leu
210                 215                 220

Gly Asn Leu Asp Asn Asn Ser Leu Lys Val Asn Met Phe Asn Pro Thr
225                 230                 235                 240

Leu Glu Ala Gln Tyr Ile Arg Leu Tyr Pro Val Ser Cys His Arg Gly
                245                 250                 255

Cys Thr Leu Arg Phe Glu Leu Leu Gly Cys Glu Leu His Gly Cys Leu
            260                 265                 270

Glu Pro Leu Gly Leu Lys Asn Asn Thr Ile Pro Asp Ser Gln Met Ser
        275                 280                 285

Ala Ser Ser Ser Tyr Lys Thr Trp Asn Leu Arg Ala Phe Gly Trp Tyr
    290                 295                 300

Pro His Leu Gly Arg Leu Asp Asn Gln Gly Lys Ile Asn Ala Trp Thr
305                 310                 315                 320

Ala Gln Ser Asn Ser Ala Lys Glu Trp Leu Gln Val Asp Leu Gly Thr
                325                 330                 335

Gln Arg Gln Val Thr Gly Ile Ile Thr Gln Gly Ala Arg Asp Phe Gly
            340                 345                 350

His Ile Gln Tyr Val Glu Ser Tyr Lys Val Ala His Ser Asp Asp Gly
        355                 360                 365

Val Gln Trp Thr Val Tyr Glu Glu Gln Gly Ser Ser Lys Val Phe Gln
    370                 375                 380

Gly Asn Leu Asp Asn Asn Ser His Lys Lys Asn Ile Phe Glu Lys Pro
385                 390                 395                 400

Phe Met Ala Arg Tyr Val Arg Val Leu Pro Val Ser Trp His Asn Arg
                405                 410                 415

Ile Thr Leu Arg Leu Glu Leu Leu Gly Cys Thr Gly His His His
            420                 425                 430

His His

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer
      LTDNf22

<400> SEQUENCE: 11
ccctcgtaca cctgcacgtg cc                                              22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer
      LTDNf23

<400> SEQUENCE: 12
cccacgagct gccacacggc c                                               21
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer
      LTDNf24

<400> SEQUENCE: 13
aaatgtgtcg agccactggg c                                          21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer
      LTDNf25

<400> SEQUENCE: 14
ggatgcgcca atcccctgg                                             19

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Primer
      LTDNr26

<400> SEQUENCE: 15
gaaggaaccg gtacagccca gtagctcaaa gcg                             33

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer
      LTDNf30

<400> SEQUENCE: 16
ggatgttcta cacagctggg ca                                         22

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Primer
      LTDNf31

<400> SEQUENCE: 17
accgaataca tctgcca                                               17

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer
      LTDNf32

<400> SEQUENCE: 18
cctgtttcgt gccaccgcgg c                                          21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer
      LTDNf33

<400> SEQUENCE: 19
ggatgtctcg agcccctgg                                                      19

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Primer
      IL2f1

<400> SEQUENCE: 20
aggaggaagc ttatgtacag gatgcaactc c                                        31

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Primer
      IL2r2

<400> SEQUENCE: 21
agtcagtgtt gagatgatg                                                      19

<210> SEQ ID NO 22
<211> LENGTH: 318
<212> TYPE: PRT
<213> ORGANISM: Artificial Sequence
<220> FEATURE:
<223> OTHER INFORMATION: Description of Artificial Sequence: His/IL2-hC1

<400> SEQUENCE: 22

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Lys Cys Val Glu Pro Leu Gly
145                 150                 155                 160

```
Met Glu Asn Gly Asn Ile Ala Asn Ser Gln Ile Ala Ala Ser Ser Val
            165                 170                 175

Arg Val Thr Phe Leu Gly Leu Gln His Trp Val Pro Glu Leu Ala Arg
        180                 185                 190

Leu Asn Arg Ala Gly Met Val Asn Ala Trp Thr Pro Ser Ser Asn Asp
    195                 200                 205

Asp Asn Pro Trp Ile Gln Val Asn Leu Leu Arg Met Trp Val Thr
210                 215                 220

Gly Val Val Thr Gln Gly Ala Ser Arg Leu Ala Ser His Glu Tyr Leu
225                 230                 235                 240

Lys Ala Phe Lys Val Ala Tyr Ser Leu Asn Gly His Glu Phe Asp Phe
                245                 250                 255

Ile His Asp Val Asn Lys Lys His Lys Glu Phe Val Gly Asn Trp Asn
            260                 265                 270

Lys Asn Ala Val His Val Asn Leu Phe Glu Thr Pro Val Glu Ala Gln
        275                 280                 285

Tyr Val Arg Leu Tyr Pro Thr Ser Cys His Thr Ala Cys Thr Leu Arg
    290                 295                 300

Phe Glu Leu Leu Gly Cys Thr Gly His His His His His
305                 310                 315

<210> SEQ ID NO 23
<211> LENGTH: 336
<212> TYPE: PRT
<213> ORGANISM: Artificial Sequence
<220> FEATURE:
<223> OTHER INFORMATION: Description of Artificial Sequence:
      His/IL2-extended hC1

<400> SEQUENCE: 23

Met Tyr Arg Met Gln Leu Leu Ser Cys Ile Ala Leu Ser Leu Ala Leu
  1               5                  10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Pro Ser Tyr Thr Cys Thr Cys
145                 150                 155                 160

Leu Lys Gly Tyr Ala Gly Asn His Cys Glu Thr Lys Cys Val Glu Pro
                165                 170                 175

Leu Gly Met Glu Asn Gly Asn Ile Ala Asn Ser Gln Ile Ala Ala Ser
            180                 185                 190

Ser Val Arg Val Thr Phe Leu Gly Leu Gln His Trp Val Pro Glu Leu
        195                 200                 205
```

```
Ala Arg Leu Asn Arg Ala Gly Met Val Asn Ala Trp Thr Pro Ser Ser
    210                 215                 220

Asn Asp Asp Asn Pro Trp Ile Gln Val Asn Leu Leu Arg Arg Met Trp
225                 230                 235                 240

Val Thr Gly Val Val Thr Gln Gly Ala Ser Arg Leu Ala Ser His Glu
                245                 250                 255

Tyr Leu Lys Ala Phe Lys Val Ala Tyr Ser Leu Asn Gly His Glu Phe
            260                 265                 270

Asp Phe Ile His Asp Val Asn Lys Lys His Lys Glu Phe Val Gly Asn
        275                 280                 285

Trp Asn Lys Asn Ala Val His Val Asn Leu Phe Glu Thr Pro Val Glu
290                 295                 300

Ala Gln Tyr Val Arg Leu Tyr Pro Thr Ser Cys His Thr Ala Cys Thr
305                 310                 315                 320

Leu Arg Phe Glu Leu Leu Gly Cys Thr Gly His His His His His
            325                 330                 335

<210> SEQ ID NO 24
<211> LENGTH: 320
<212> TYPE: PRT
<213> ORGANISM: Artificial Sequence
<220> FEATURE:
<223> OTHER INFORMATION: Description of Artificial Sequence: His/IL2-hC2

<400> SEQUENCE: 24

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Cys Ala Asn Pro Leu Gly
145                 150                 155                 160

Leu Lys Asn Asn Ser Ile Pro Asp Lys Gln Ile Thr Ala Ser Ser Ser
                165                 170                 175

Tyr Lys Thr Trp Gly Leu His Leu Phe Ser Trp Asn Pro Ser Tyr Ala
            180                 185                 190

Arg Leu Asp Lys Gln Gly Asn Phe Asn Ala Trp Val Ala Gly Ser Tyr
        195                 200                 205

Gly Asn Asp Gln Trp Leu Gln Val Asp Leu Gly Ser Ser Lys Glu Val
    210                 215                 220

Thr Gly Ile Ile Thr Gln Gly Ala Arg Asn Phe Gly Ser Val Gln Phe
225                 230                 235                 240
```

Val Ala Ser Tyr Lys Val Ala Tyr Ser Asn Asp Ser Ala Asn Trp Thr
            245                 250                 255

Glu Tyr Gln Asp Pro Arg Thr Gly Ser Ser Lys Ile Phe Pro Gly Asn
        260                 265                 270

Trp Asp Asn His Ser His Lys Lys Asn Leu Phe Glu Thr Pro Ile Leu
    275                 280                 285

Ala Arg Tyr Val Arg Ile Leu Pro Val Ala Trp His Asn Arg Ile Ala
290                 295                 300

Leu Arg Leu Glu Leu Leu Gly Cys Thr Gly His His His His His His
305                 310                 315                 320

<210> SEQ ID NO 25
<211> LENGTH: 340
<212> TYPE: PRT
<213> ORGANISM: Artificial Sequence
<220> FEATURE:
<223> OTHER INFORMATION: Description of Artificial Sequence:
      His/IL2-extended hC2

<400> SEQUENCE: 25

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Pro Thr Ser Cys His Thr Ala
145                 150                 155                 160

Cys Thr Leu Arg Phe Glu Leu Leu Gly Cys Glu Leu Asn Gly Cys Ala
                165                 170                 175

Asn Pro Leu Gly Leu Lys Asn Asn Ser Ile Pro Asp Lys Gln Ile Thr
            180                 185                 190

Ala Ser Ser Ser Tyr Lys Thr Trp Gly Leu His Leu Phe Ser Trp Asn
        195                 200                 205

Pro Ser Tyr Ala Arg Leu Asp Lys Gln Gly Asn Phe Asn Ala Trp Val
210                 215                 220

Ala Gly Ser Tyr Gly Asn Asp Gln Trp Leu Gln Val Asp Leu Gly Ser
225                 230                 235                 240

Ser Lys Glu Val Thr Gly Ile Ile Thr Gln Gly Ala Arg Asn Phe Gly
                245                 250                 255

Ser Val Gln Phe Val Ala Ser Tyr Lys Val Ala Tyr Ser Asn Asp Ser
            260                 265                 270

Ala Asn Trp Thr Glu Tyr Gln Asp Pro Arg Thr Gly Ser Ser Lys Ile

```
                    275             280             285
Phe Pro Gly Asn Trp Asp Asn His Ser His Lys Lys Asn Leu Phe Glu
    290                 295                 300
Thr Pro Ile Leu Ala Arg Tyr Val Arg Ile Leu Pro Val Ala Trp His
305                 310                 315                 320
Asn Arg Ile Ala Leu Arg Leu Glu Leu Leu Gly Cys Thr Gly His His
                325                 330                 335
His His His His
        340

<210> SEQ ID NO 26
<211> LENGTH: 480
<212> TYPE: PRT
<213> ORGANISM: Artificial Sequence
<220> FEATURE:
<223> OTHER INFORMATION: Description of Artificial Sequence:
      His/IL2-hC1/C2

<400> SEQUENCE: 26

Met Tyr Arg Met Gln Leu Leu Ser Cys Ile Ala Leu Ser Leu Ala Leu
 1               5                  10                  15
Val Thr Asn Ser Ala Pro Thr Ser Ser Ser Thr Lys Lys Thr Gln Leu
                20                  25                  30
Gln Leu Glu His Leu Leu Leu Asp Leu Gln Met Ile Leu Asn Gly Ile
            35                  40                  45
Asn Asn Tyr Lys Asn Pro Lys Leu Thr Arg Met Leu Thr Phe Lys Phe
        50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
    130                 135                 140
Cys Gln Ser Ile Ile Ser Thr Leu Thr Lys Cys Val Glu Pro Leu Gly
145                 150                 155                 160
Met Glu Asn Gly Asn Ile Ala Asn Ser Gln Ile Ala Ala Ser Ser Val
                165                 170                 175
Arg Val Thr Phe Leu Gly Leu Gln His Trp Val Pro Glu Leu Ala Arg
            180                 185                 190
Leu Asn Arg Ala Gly Met Val Asn Ala Trp Thr Pro Ser Ser Asn Asp
        195                 200                 205
Asp Asn Pro Trp Ile Gln Val Asn Leu Leu Arg Arg Met Trp Val Thr
    210                 215                 220
Gly Val Val Thr Gln Gly Ala Ser Arg Leu Ala Ser His Glu Tyr Leu
225                 230                 235                 240
Lys Ala Phe Lys Val Ala Tyr Ser Leu Asn Gly His Glu Phe Asp Phe
                245                 250                 255
Ile His Asp Val Asn Lys Lys His Lys Glu Phe Val Gly Asn Trp Asn
            260                 265                 270
Lys Asn Ala Val His Val Asn Leu Phe Glu Thr Pro Val Glu Ala Gln
        275                 280                 285
```

-continued

```
Tyr Val Arg Leu Tyr Pro Thr Ser Cys His Thr Ala Cys Thr Leu Arg
    290                 295                 300

Phe Glu Leu Leu Gly Cys Glu Leu Asn Gly Cys Ala Asn Pro Leu Gly
305                 310                 315                 320

Leu Lys Asn Asn Ser Ile Pro Asp Lys Gln Ile Thr Ala Ser Ser Ser
                325                 330                 335

Tyr Lys Thr Trp Gly Leu His Leu Phe Ser Trp Asn Pro Ser Tyr Ala
            340                 345                 350

Arg Leu Asp Lys Gln Gly Asn Phe Asn Ala Trp Val Ala Gly Ser Tyr
        355                 360                 365

Gly Asn Asp Gln Trp Leu Gln Val Asp Leu Gly Ser Ser Lys Glu Val
    370                 375                 380

Thr Gly Ile Ile Thr Gln Gly Ala Arg Asn Phe Gly Ser Val Gln Phe
385                 390                 395                 400

Val Ala Ser Tyr Lys Val Ala Tyr Ser Asn Asp Ser Ala Asn Trp Thr
                405                 410                 415

Glu Tyr Gln Asp Pro Arg Thr Gly Ser Ser Lys Ile Phe Pro Gly Asn
            420                 425                 430

Trp Asp Asn His Ser His Lys Lys Asn Leu Phe Glu Thr Pro Ile Leu
        435                 440                 445

Ala Arg Tyr Val Arg Ile Leu Pro Val Ala Trp His Asn Arg Ile Ala
    450                 455                 460

Leu Arg Leu Glu Leu Leu Gly Cys Thr Gly His His His His His His
465                 470                 475                 480

<210> SEQ ID NO 27
<211> LENGTH: 498
<212> TYPE: PRT
<213> ORGANISM: Artificial Sequence
<220> FEATURE:
<223> OTHER INFORMATION: Description of Artificial Sequence:
      His/IL2-extended hC1/C2

<400> SEQUENCE: 27

Met Tyr Arg Met Gln Leu Leu Ser Cys Ile Ala Leu Ser Leu Ala Leu
  1               5                  10                  15

Val Thr Asn Ser Ala Pro Thr Ser Ser Ser Thr Lys Lys Thr Gln Leu
                 20                  25                  30

Gln Leu Glu His Leu Leu Leu Asp Leu Gln Met Ile Leu Asn Gly Ile
             35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Pro Ser Tyr Thr Cys Thr Cys
145                 150                 155                 160

Leu Lys Gly Tyr Ala Gly Asn His Cys Glu Thr Lys Cys Val Glu Pro
                165                 170                 175
```

```
Leu Gly Met Glu Asn Gly Asn Ile Ala Asn Ser Gln Ile Ala Ala Ser
            180                 185                 190

Ser Val Arg Val Thr Phe Leu Gly Leu Gln His Trp Val Pro Glu Leu
        195                 200                 205

Ala Arg Leu Asn Arg Ala Gly Met Val Asn Ala Trp Thr Pro Ser Ser
    210                 215                 220

Asn Asp Asp Asn Pro Trp Ile Gln Val Asn Leu Leu Arg Arg Met Trp
225                 230                 235                 240

Val Thr Gly Val Val Thr Gln Gly Ala Ser Arg Leu Ala Ser His Glu
                245                 250                 255

Tyr Leu Lys Ala Phe Lys Val Ala Tyr Ser Leu Asn Gly His Glu Phe
            260                 265                 270

Asp Phe Ile His Asp Val Asn Lys His Lys Glu Phe Val Gly Asn
        275                 280                 285

Trp Asn Lys Asn Ala Val His Val Asn Leu Phe Glu Thr Pro Val Glu
    290                 295                 300

Ala Gln Tyr Val Arg Leu Tyr Pro Thr Ser Cys His Thr Ala Cys Thr
305                 310                 315                 320

Leu Arg Phe Glu Leu Leu Gly Cys Glu Leu Asn Gly Cys Ala Asn Pro
                325                 330                 335

Leu Gly Leu Lys Asn Asn Ser Ile Pro Asp Lys Gln Ile Thr Ala Ser
            340                 345                 350

Ser Ser Tyr Lys Thr Trp Gly Leu His Leu Phe Ser Trp Asn Pro Ser
        355                 360                 365

Tyr Ala Arg Leu Asp Lys Gln Gly Asn Phe Asn Ala Trp Val Ala Gly
    370                 375                 380

Ser Tyr Gly Asn Asp Gln Trp Leu Gln Val Asp Leu Gly Ser Ser Lys
385                 390                 395                 400

Glu Val Thr Gly Ile Ile Thr Gln Gly Ala Arg Asn Phe Gly Ser Val
                405                 410                 415

Gln Phe Val Ala Ser Tyr Lys Val Ala Tyr Ser Asn Asp Ser Ala Asn
            420                 425                 430

Trp Thr Glu Tyr Gln Asp Pro Arg Thr Gly Ser Ser Lys Ile Phe Pro
        435                 440                 445

Gly Asn Trp Asp Asn His Ser His Lys Lys Asn Leu Phe Glu Thr Pro
    450                 455                 460

Ile Leu Ala Arg Tyr Val Arg Ile Leu Pro Val Ala Trp His Asn Arg
465                 470                 475                 480

Ile Ala Leu Arg Leu Glu Leu Leu Gly Cys Thr Gly His His His His
                485                 490                 495

His His
```

<210> SEQ ID NO 28
<211> LENGTH: 140
<212> TYPE: PRT
<213> ORGANISM: Artificial Sequence
<220> FEATURE:
<223> OTHER INFORMATION: Description of Artificial Sequence:
      MelanA/MART1

<400> SEQUENCE: 28

```
Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30
```

```
Leu Thr Val Ile Leu Gly Val Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro Phe Glu Gln Lys Leu Ile Ser Glu Glu Asp
        115                 120                 125

Leu Asn Met His Thr Gly His His His His His His
    130                 135                 140

<210> SEQ ID NO 29
<211> LENGTH: 261
<212> TYPE: PRT
<213> ORGANISM: Artificial Sequence
<220> FEATURE:
<223> OTHER INFORMATION: Description of Artificial Sequence: CD40L

<400> SEQUENCE: 29

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255
```

```
Gly Leu Leu Lys Leu
            260

<210> SEQ ID NO 30
<211> LENGTH: 258
<212> TYPE: PRT
<213> ORGANISM: Artificial Sequence
<220> FEATURE:
<223> OTHER INFORMATION: Description of Artificial Sequence: CD81

<400> SEQUENCE: 30

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Ser Leu Leu Tyr Leu Glu
        35                  40                  45

Leu Gly Asn Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Met Asp Asp Asp Ala Asn Asn Ala Lys
    130                 135                 140

Ala Val Val Lys Thr Phe His Glu Thr Leu Asn Cys Cys Gly Ser Asn
145                 150                 155                 160

Ala Leu Thr Thr Leu Thr Thr Thr Ile Leu Arg Asn Thr Leu Cys Pro
                165                 170                 175

Ser Gly Gly Asn Ile Leu Thr Pro Leu Leu Gln Gln Asp Cys His Gln
            180                 185                 190

Lys Ile Asp Glu Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr Phe Glu Gln Lys
225                 230                 235                 240

Leu Ile Ser Glu Glu Asp Leu Asn Met His Thr Gly His His His His
                245                 250                 255

His His

<210> SEQ ID NO 31
<211> LENGTH: 222
<212> TYPE: PRT
<213> ORGANISM: Artificial Sequence
<220> FEATURE:
<223> OTHER INFORMATION: Description of Artificial Sequence: CD81E

<400> SEQUENCE: 31

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30
```

Leu Trp Leu Arg His Asp Pro Gln Thr Thr Ser Leu Leu Tyr Leu Glu
           35                  40                  45

Leu Gly Asn Lys Pro Ala Pro Asn Thr Phe Tyr Val Gly Ile Tyr Ile
     50                  55                  60

Leu Ile Ala Val Gly Ala Val Met Met Phe Val Gly Phe Leu Gly Cys
 65                  70                  75                  80

Tyr Gly Ala Ile Gln Glu Ser Gln Cys Leu Leu Gly Thr Phe Phe Thr
                 85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Met Asp Asp Asp Ala Asn Asn Ala Lys
130                 135                 140

Ala Val Val Lys Thr Phe His Glu Thr Leu Asn Cys Cys Gly Ser Asn
145                 150                 155                 160

Ala Leu Thr Thr Leu Thr Thr Thr Ile Leu Arg Asn Thr Leu Cys Pro
                165                 170                 175

Ser Gly Gly Asn Ile Leu Thr Pro Leu Leu Gln Gln Asp Cys His Gln
            180                 185                 190

Lys Ile Asp Glu Leu Phe Ser Gly Phe Glu Gln Lys Leu Ile Ser Glu
        195                 200                 205

Glu Asp Leu Asn Met His Thr Gly His His His His His His
210                 215                 220

<210> SEQ ID NO 32
<211> LENGTH: 496
<212> TYPE: PRT
<213> ORGANISM: Artificial Sequence
<220> FEATURE:
<223> OTHER INFORMATION: Description of Artificial Sequence: MART1/CCR7

<400> SEQUENCE: 32

Met Pro Arg Glu Asp Ala His Phe Ile Tyr Gly Tyr Pro Lys Lys Gly
 1               5                  10                  15

His Gly His Ser Tyr Thr Thr Ala Glu Glu Ala Ala Gly Ile Gly Ile
             20                  25                  30

Leu Thr Val Ile Leu Gly Val Leu Leu Leu Ile Gly Cys Trp Tyr Cys
         35                  40                  45

Arg Arg Arg Asn Gly Tyr Arg Ala Leu Met Asp Lys Ser Leu His Val
     50                  55                  60

Gly Thr Gln Cys Ala Leu Thr Arg Arg Cys Pro Gln Glu Gly Phe Asp
 65                  70                  75                  80

His Arg Asp Ser Lys Val Ser Leu Gln Glu Lys Asn Cys Glu Pro Val
                 85                  90                  95

Val Pro Asn Ala Pro Pro Ala Tyr Glu Lys Leu Ser Ala Glu Gln Ser
            100                 105                 110

Pro Pro Pro Tyr Ser Pro Phe Glu Gln Lys Leu Ile Ser Glu Glu Asp
        115                 120                 125

Leu Asn Met His Thr Gly Gln Asp Glu Val Thr Asp Asp Tyr Ile Gly
130                 135                 140

Asp Asn Thr Thr Val Asp Tyr Thr Leu Phe Glu Ser Leu Cys Ser Lys
145                 150                 155                 160

Lys Asp Val Arg Asn Phe Lys Ala Trp Phe Leu Pro Ile Met Tyr Ser
                165                 170                 175

```
Ile Ile Cys Phe Val Gly Leu Leu Gly Asn Gly Leu Val Val Leu Thr
            180                 185                 190

Tyr Ile Tyr Phe Lys Arg Leu Lys Thr Met Thr Asp Thr Tyr Leu Leu
        195                 200                 205

Asn Leu Ala Val Ala Asp Ile Leu Phe Leu Leu Thr Leu Pro Phe Trp
        210                 215                 220

Ala Tyr Ser Ala Ala Lys Ser Trp Val Phe Gly Val His Phe Cys Lys
225                 230                 235                 240

Leu Ile Phe Ala Ile Tyr Lys Met Ser Phe Phe Ser Gly Met Leu Leu
                245                 250                 255

Leu Leu Cys Ile Ser Ile Asp Arg Tyr Val Ala Ile Val Gln Ala Val
            260                 265                 270

Ser Ala His Arg His Arg Ala Arg Val Leu Leu Ile Ser Lys Leu Ser
        275                 280                 285

Cys Val Gly Ile Trp Ile Leu Ala Thr Val Leu Ser Ile Pro Glu Leu
        290                 295                 300

Leu Tyr Ser Asp Leu Gln Arg Ser Ser Glu Gln Ala Met Arg Cys
305                 310                 315                 320

Ser Leu Ile Thr Glu His Val Glu Ala Phe Ile Thr Ile Gln Val Ala
                325                 330                 335

Gln Met Val Ile Gly Phe Leu Val Pro Leu Leu Ala Met Ser Phe Cys
            340                 345                 350

Tyr Leu Val Ile Ile Arg Thr Leu Leu Gln Ala Arg Asn Phe Glu Arg
        355                 360                 365

Asn Lys Ala Ile Lys Val Ile Ile Ala Val Val Val Val Phe Ile Val
        370                 375                 380

Phe Gln Leu Pro Tyr Asn Gly Val Val Leu Ala Gln Thr Val Ala Asn
385                 390                 395                 400

Phe Asn Ile Thr Ser Ser Thr Cys Glu Leu Ser Lys Gln Leu Asn Ile
                405                 410                 415

Ala Tyr Asp Val Thr Tyr Ser Leu Ala Cys Val Arg Cys Cys Val Asn
            420                 425                 430

Pro Phe Leu Tyr Ala Phe Ile Gly Val Lys Phe Arg Asn Asp Leu Phe
        435                 440                 445

Lys Leu Phe Lys Asp Leu Gly Cys Leu Ser Gln Glu Gln Leu Arg Gln
        450                 455                 460

Trp Ser Ser Cys Arg His Ile Arg Arg Ser Ser Met Ser Val Glu Ala
465                 470                 475                 480

Glu Thr Thr Thr Thr Phe Ser Pro Thr Gly His His His His His His
                485                 490                 495

<210> SEQ ID NO 33
<211> LENGTH: 578
<212> TYPE: PRT
<213> ORGANISM: Artificial Sequence
<220> FEATURE:
<223> OTHER INFORMATION: Description of Artificial Sequence: CD81E/CCR7

<400> SEQUENCE: 33

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Ser Leu Leu Tyr Leu Glu
        35                  40                  45
```

```
Leu Gly Asn Lys Pro Ala Pro Asn Thr Phe Tyr Val Gly Ile Tyr Ile
         50                  55                  60

Leu Ile Ala Val Gly Ala Val Met Met Phe Val Gly Phe Leu Gly Cys
 65                  70                  75                  80

Tyr Gly Ala Ile Gln Glu Ser Gln Cys Leu Leu Gly Thr Phe Phe Thr
                 85                  90                  95

Cys Leu Val Ile Leu Phe Ala Cys Glu Val Ala Ala Gly Ile Trp Gly
                100                 105                 110

Phe Val Asn Lys Asp Gln Ile Ala Lys Asp Val Lys Gln Phe Tyr Asp
                115                 120                 125

Gln Ala Leu Gln Gln Ala Val Met Asp Asp Ala Asn Asn Ala Lys
        130                 135                 140

Ala Val Val Lys Thr Phe His Glu Thr Leu Asn Cys Cys Gly Ser Asn
145                 150                 155                 160

Ala Leu Thr Thr Leu Thr Thr Thr Ile Leu Arg Asn Thr Leu Cys Pro
                165                 170                 175

Ser Gly Gly Asn Ile Leu Thr Pro Leu Leu Gln Gln Asp Cys His Gln
                180                 185                 190

Lys Ile Asp Glu Leu Phe Ser Gly Phe Glu Gln Lys Leu Ile Ser Glu
                195                 200                 205

Glu Asp Leu Asn Met His Thr Gly Gln Asp Glu Val Thr Asp Asp Tyr
210                 215                 220

Ile Gly Asp Asn Thr Thr Val Asp Tyr Thr Leu Phe Glu Ser Leu Cys
225                 230                 235                 240

Ser Lys Lys Asp Val Arg Asn Phe Lys Ala Trp Phe Leu Pro Ile Met
                245                 250                 255

Tyr Ser Ile Ile Cys Phe Val Gly Leu Leu Gly Asn Gly Leu Val Val
                260                 265                 270

Leu Thr Tyr Ile Tyr Phe Lys Arg Leu Lys Thr Met Thr Asp Thr Tyr
                275                 280                 285

Leu Leu Asn Leu Ala Val Ala Asp Ile Leu Phe Leu Leu Thr Leu Pro
        290                 295                 300

Phe Trp Ala Tyr Ser Ala Ala Lys Ser Trp Val Phe Gly Val His Phe
305                 310                 315                 320

Cys Lys Leu Ile Phe Ala Ile Tyr Lys Met Ser Phe Phe Ser Gly Met
                325                 330                 335

Leu Leu Leu Leu Cys Ile Ser Ile Asp Arg Tyr Val Ala Ile Val Gln
                340                 345                 350

Ala Val Ser Ala His Arg His Arg Ala Arg Val Leu Leu Ile Ser Lys
                355                 360                 365

Leu Ser Cys Val Gly Ile Trp Ile Leu Ala Thr Val Leu Ser Ile Pro
        370                 375                 380

Glu Leu Leu Tyr Ser Asp Leu Gln Arg Ser Ser Ser Glu Gln Ala Met
385                 390                 395                 400

Arg Cys Ser Leu Ile Thr Glu His Val Glu Ala Phe Ile Thr Ile Gln
                405                 410                 415

Val Ala Gln Met Val Ile Gly Phe Leu Val Pro Leu Leu Ala Met Ser
                420                 425                 430

Phe Cys Tyr Leu Val Ile Ile Arg Thr Leu Leu Gln Ala Arg Asn Phe
        435                 440                 445

Glu Arg Asn Lys Ala Ile Lys Val Ile Ile Ala Val Val Val Val Phe
450                 455                 460
```

-continued

```
Ile Val Phe Gln Leu Pro Tyr Asn Gly Val Val Leu Ala Gln Thr Val
465                 470                 475                 480

Ala Asn Phe Asn Ile Thr Ser Ser Thr Cys Glu Leu Ser Lys Gln Leu
                485                 490                 495

Asn Ile Ala Tyr Asp Val Thr Tyr Ser Leu Ala Cys Val Arg Cys Cys
            500                 505                 510

Val Asn Pro Phe Leu Tyr Ala Phe Ile Gly Val Lys Phe Arg Asn Asp
            515                 520                 525

Leu Phe Lys Leu Phe Lys Asp Leu Gly Cys Leu Ser Gln Glu Gln Leu
        530                 535                 540

Arg Gln Trp Ser Ser Cys Arg His Ile Arg Arg Ser Ser Met Ser Val
545                 550                 555                 560

Glu Ala Glu Thr Thr Thr Thr Phe Ser Pro Thr Gly His His His His
                565                 570                 575

His His
```